US005599347A

United States Patent [19]

Hart et al.

[11] Patent Number: 5,599,347
[45] Date of Patent: *Feb. 4, 1997

[54] SURGICAL TROCAR WITH CUTOFF CIRCUIT

[75] Inventors: Charles C. Hart, Huntington Beach; Nabil Hilal, Mission Viejo; Martin V. Shabaz, Santa Ana; Mark A. Ritchart, Murrieta, all of Calif.

[73] Assignee: Applied Medical Resources Corporation, Laguna Hills, Calif.

[ * ] Notice: The term of this patent shall not extend beyond the expiration date of Pat. No. 5,344,420.

[21] Appl. No.: 303,125

[22] Filed: Sep. 7, 1994

Related U.S. Application Data

[63] Continuation of Ser. No. 45,369, Apr. 9, 1993, abandoned, which is a continuation-in-part of Ser. No. 791,878, Nov. 13, 1991, abandoned, which is a continuation-in-part of Ser. No. 654,815, Feb. 13, 1991, abandoned.

[51] Int. Cl.$^6$ ................................................ A61B 17/36
[52] U.S. Cl. .......................... 606/42; 606/41; 606/45; 604/264
[58] Field of Search .................... 606/37–42, 45–50; 604/21, 22, 264, 272

[56] References Cited

U.S. PATENT DOCUMENTS

| | | | |
|---|---|---|---|
| 1,741,461 | 12/1929 | Herman . | |
| 3,585,239 | 7/1971 | Petersen . | |
| 3,595,239 | 7/1971 | Petersen | 606/45 |
| 4,043,342 | 8/1977 | Morrison, Jr. | 606/48 |
| 4,269,174 | 5/1981 | Adair | 128/1 R |
| 4,269,192 | 5/1981 | Matsuo | 128/665 |
| 4,299,230 | 11/1981 | Kubota | 128/630 |
| 4,418,692 | 12/1983 | Guay . | |
| 4,535,773 | 8/1985 | Yoon | 604/51 |
| 4,550,727 | 11/1985 | Rexroth | 606/39 |
| 4,580,562 | 4/1986 | Goof et al. | 606/39 |
| 4,654,030 | 3/1987 | Moll et al. | 606/165 |
| 4,750,489 | 6/1988 | Berkman et al. . | |
| 4,785,807 | 11/1988 | Blanch | 606/45 |
| 4,788,977 | 12/1988 | Farin | 606/39 |
| 4,793,345 | 12/1988 | Lehmer | 606/39 |
| 4,807,620 | 2/1989 | Strul et al. . | |
| 4,850,353 | 7/1989 | Stasz et al. . | |
| 4,902,280 | 2/1990 | Lander . | |
| 4,986,814 | 1/1991 | Burney et al. . | |
| 5,009,656 | 4/1991 | Reimels . | |
| 5,057,099 | 10/1991 | Rink . | |
| 5,071,222 | 12/1991 | Laakmann . | |
| 5,300,070 | 4/1994 | Gentelia et al. | 606/45 |
| 5,344,420 | 9/1994 | Hilal et al. | 606/42 |
| 5,380,321 | 1/1995 | Yoon | 606/41 |
| 5,417,687 | 5/1995 | Nardella et al. | 604/164 |

*Primary Examiner*—Angela D. Sykes
*Assistant Examiner*—Michael Peffley
*Attorney, Agent, or Firm*—Richard L. Myers

[57] ABSTRACT

A surgical trocar includes an operative sleeve adapted for disposition across a tissue barrier and an obturator removably disposed in the sleeve. An obturator includes a cutting element which is operable to cut the tissue. The obturator and the operative sleeve can be advanced through the cut tissue and the obturator removed leaving the sleeve operatively disposed for further surgery. A cutoff and reset mechanism is responsive to a condition present when the obturator penetrates the tissue barrier to inhibit further cutting by the cutting element. A reset mechanism is manually operable through the conscious efforts of the surgeon to reset the trocar should further cutting be desired. The cutoff and reset mechanisms can be embodied mechanically as well as electrically and adapted to both mechanical and electrosurgical trocars.

41 Claims, 14 Drawing Sheets

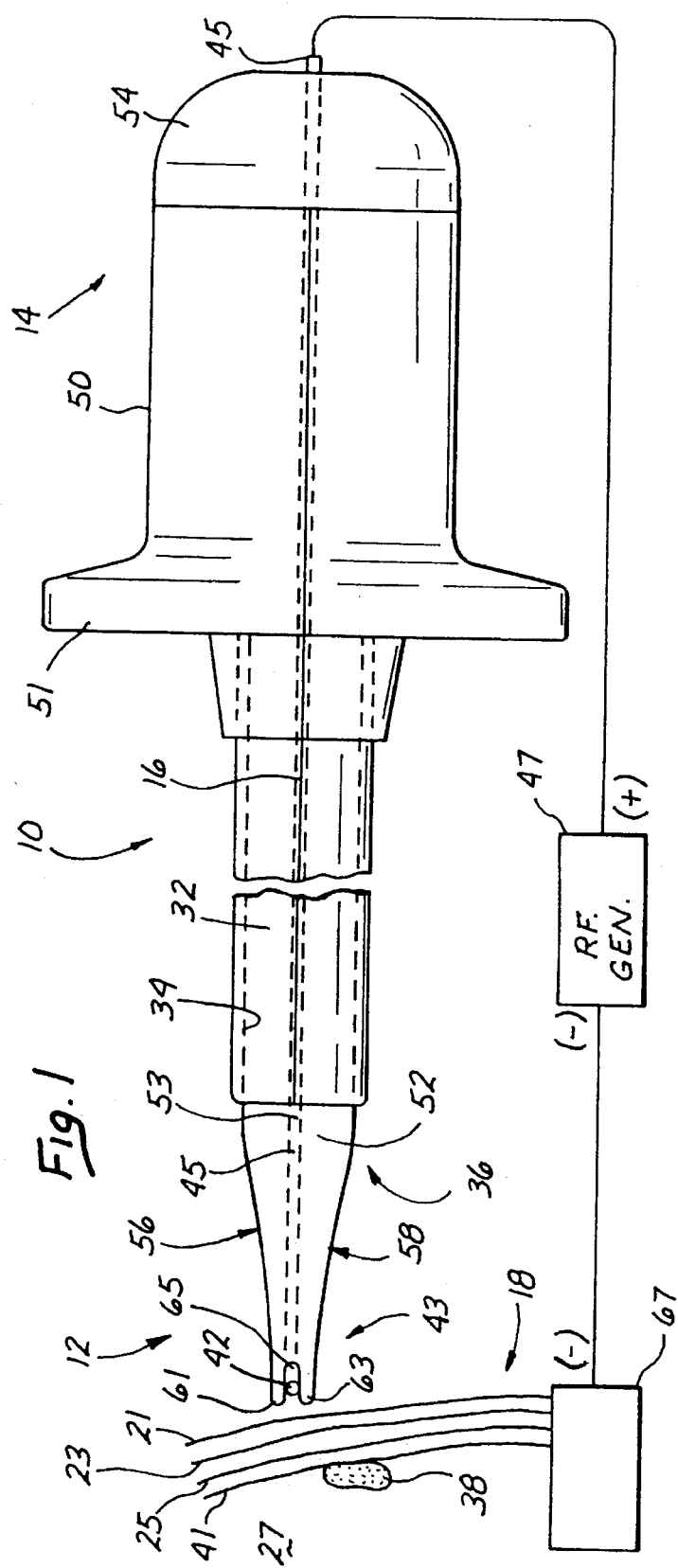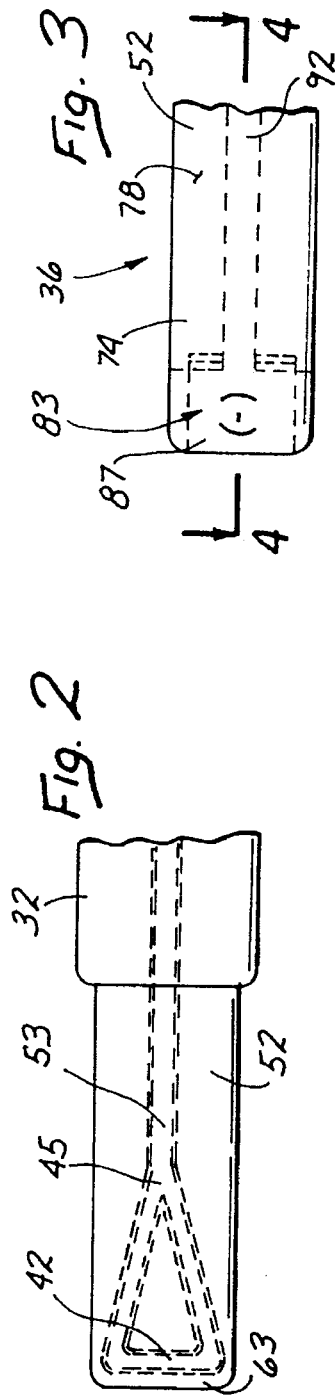

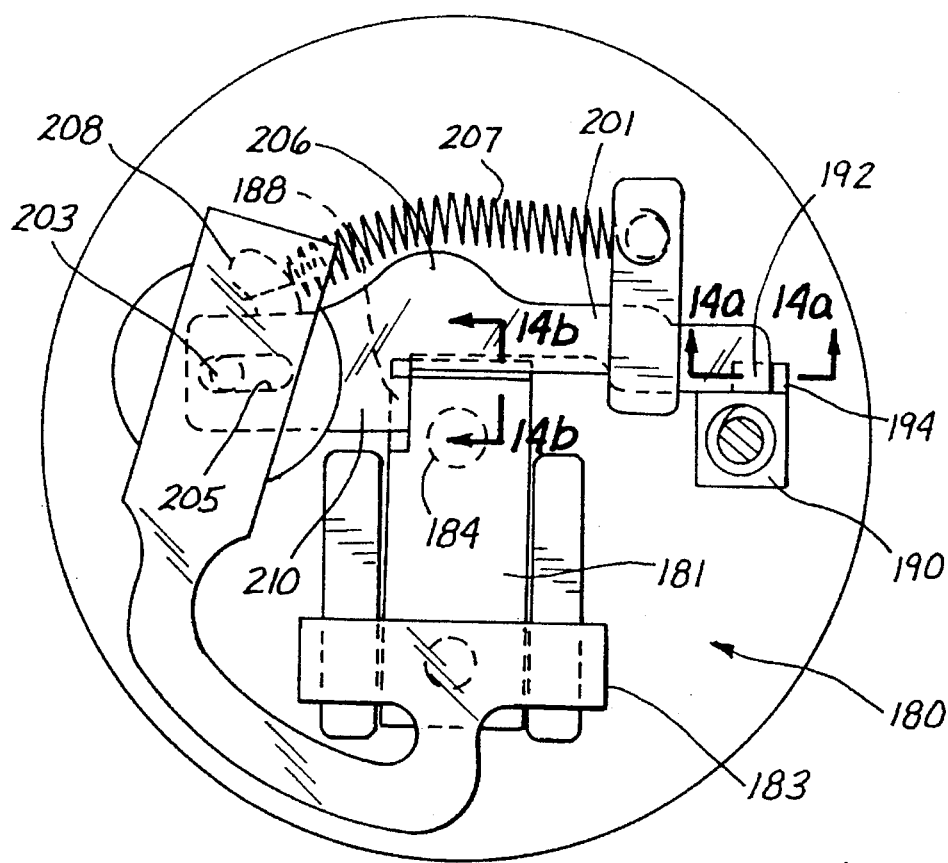
Fig. 14
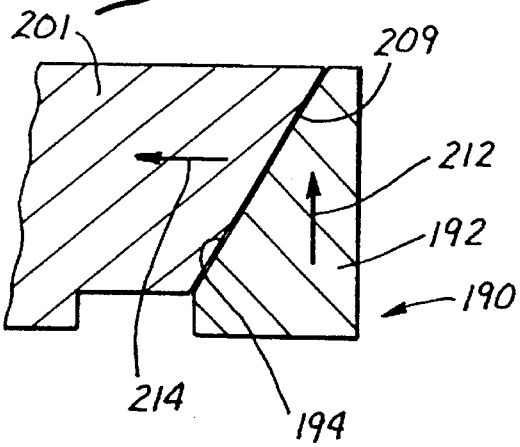
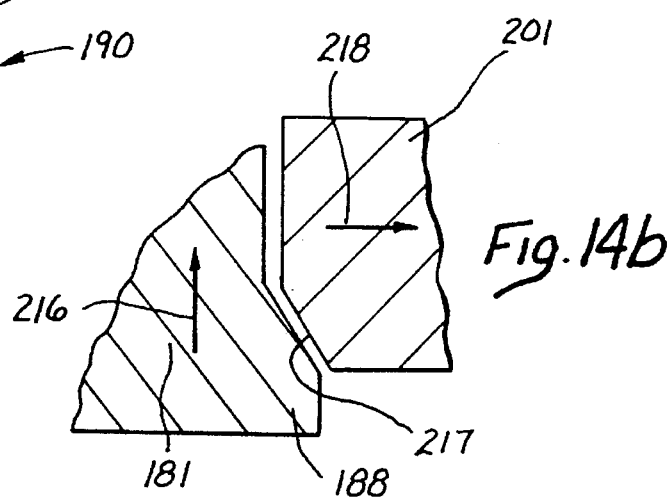

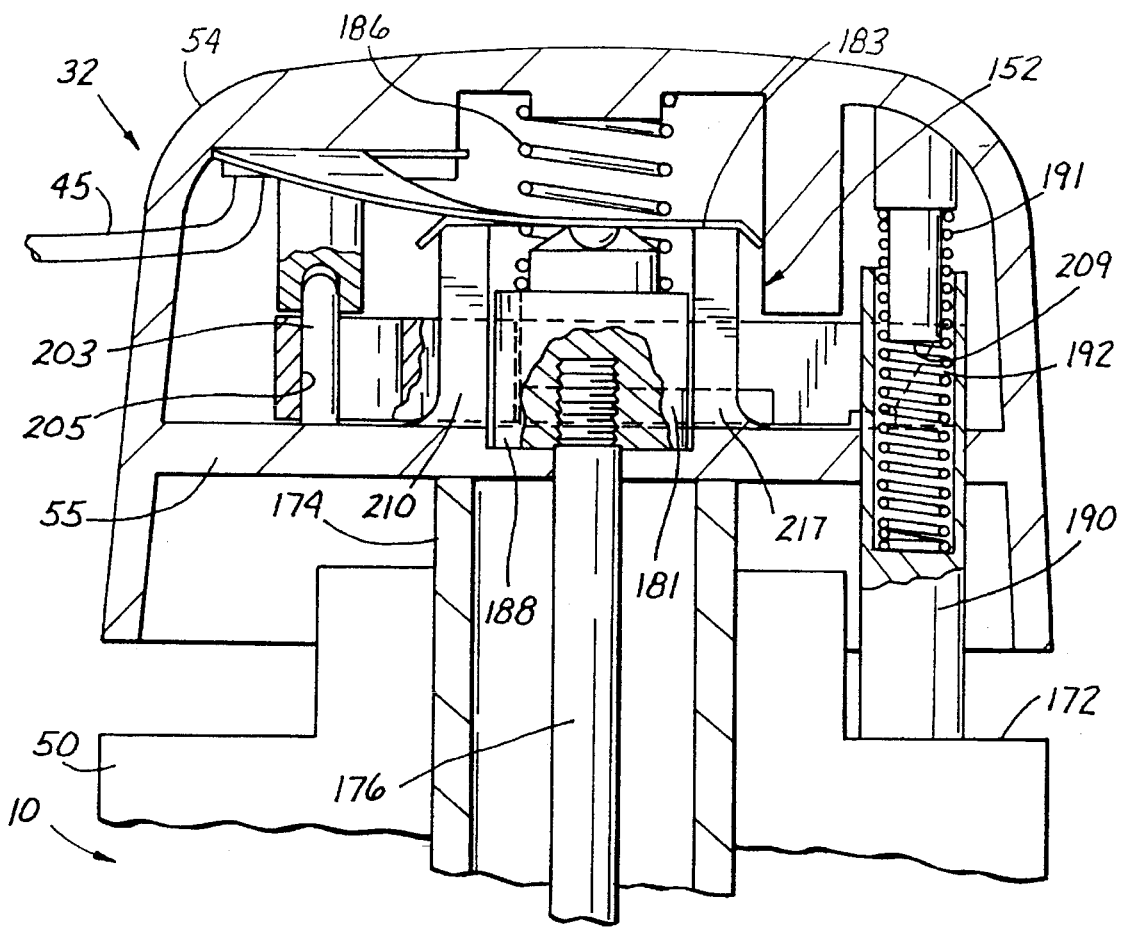
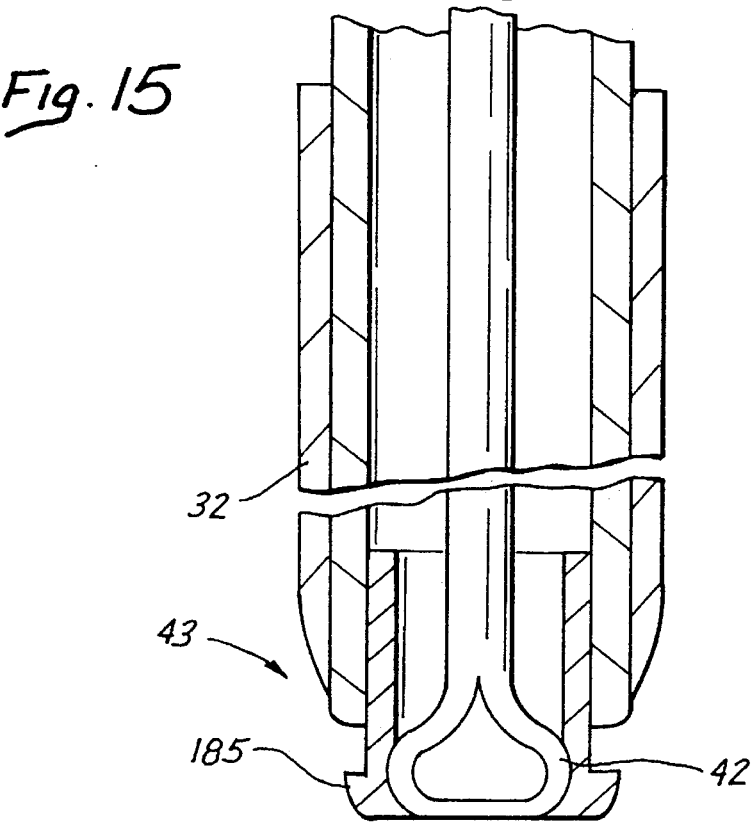
Fig. 15

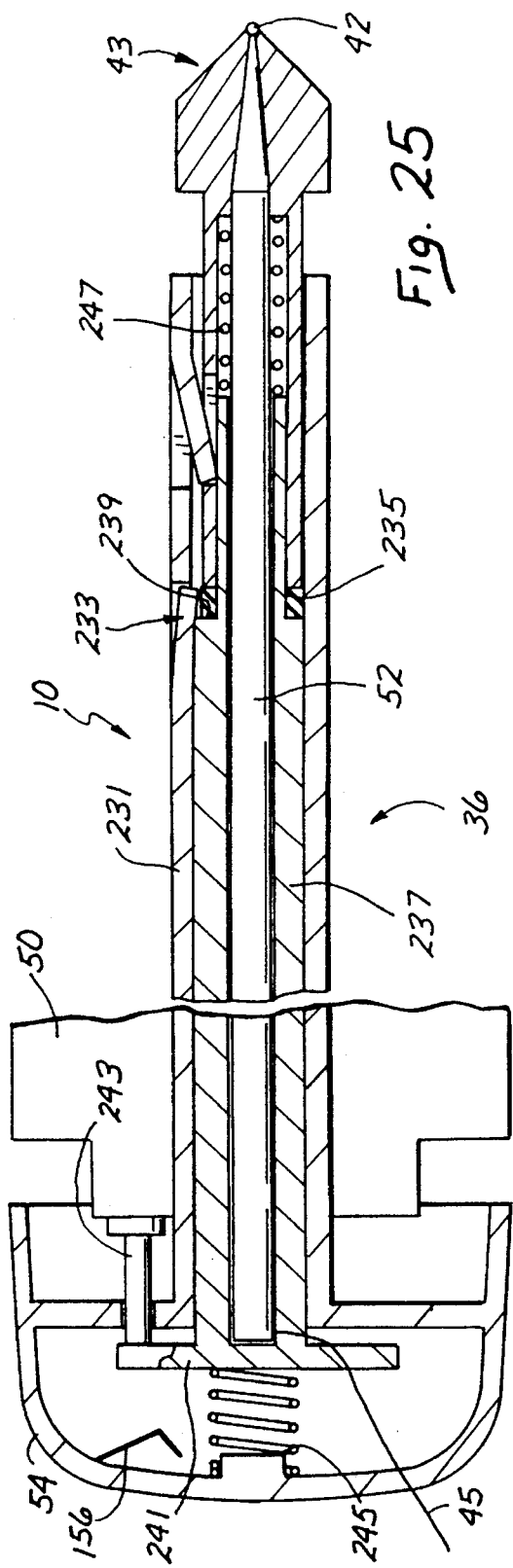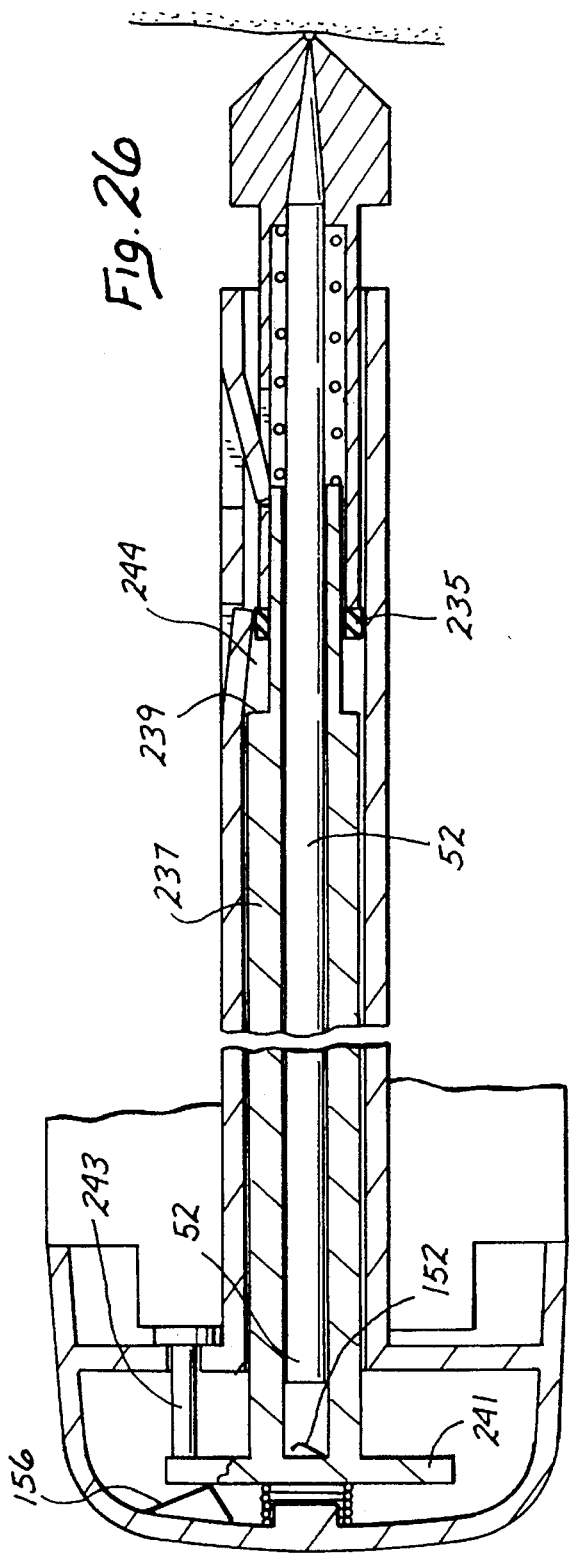

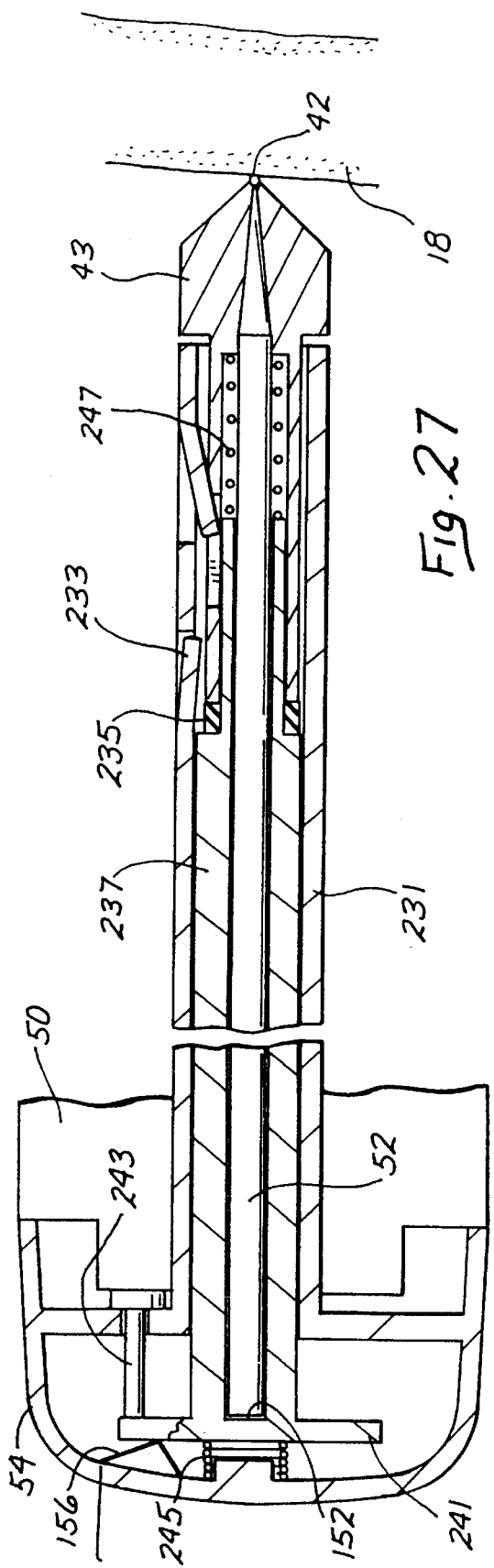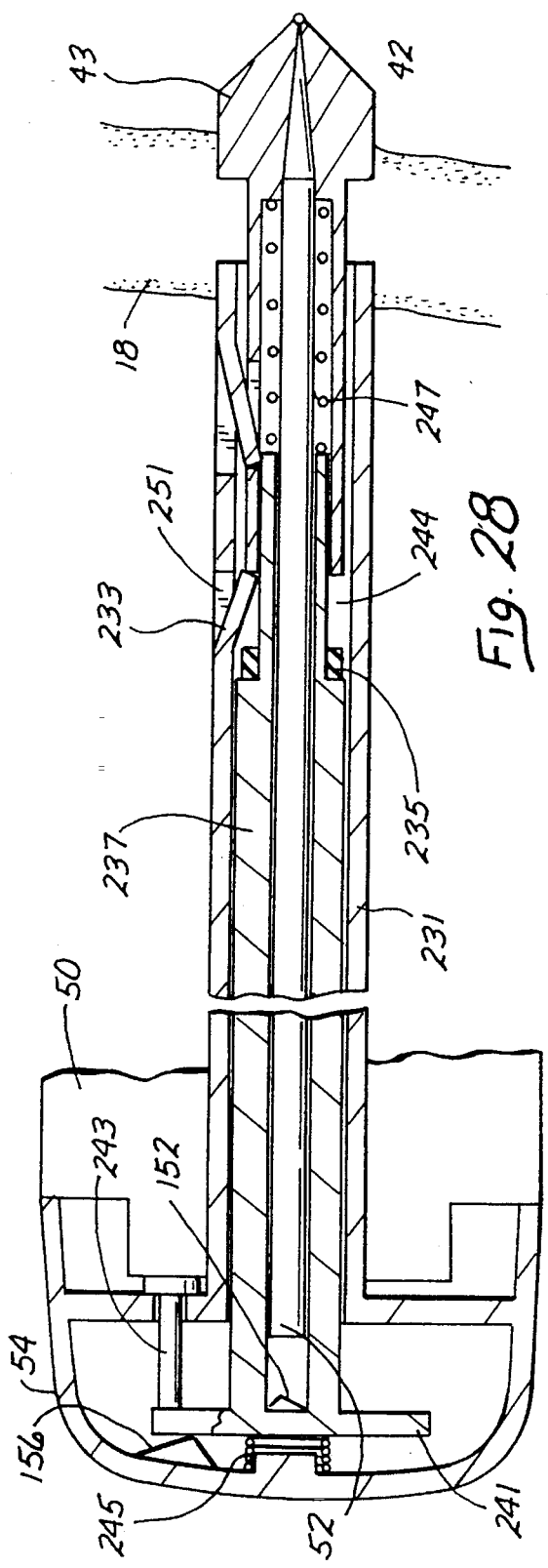

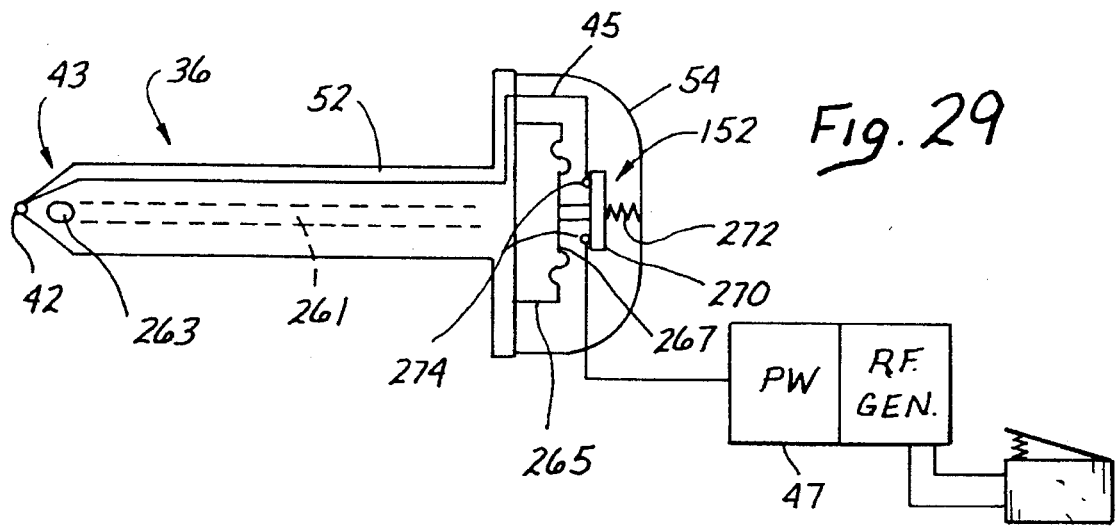
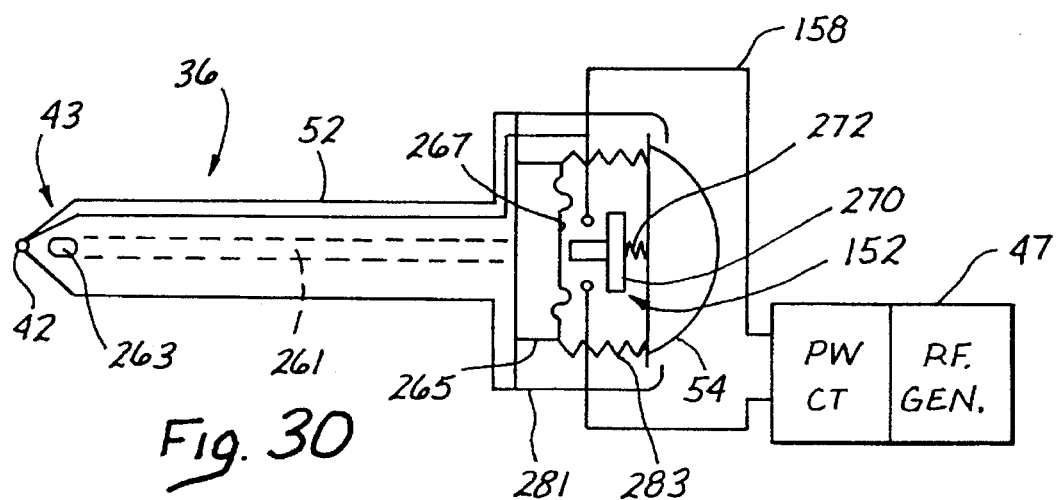
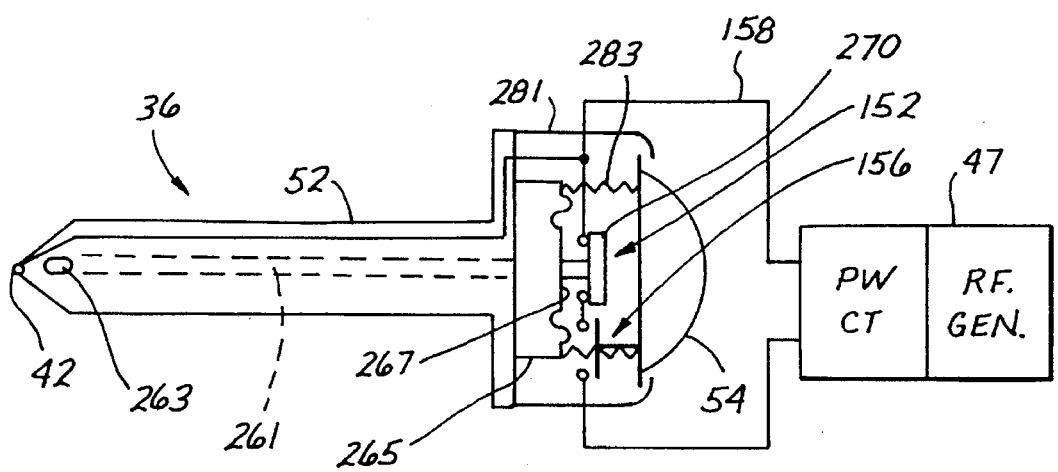

SURGICAL TROCAR WITH CUTOFF CIRCUIT

REFERENCE TO RELATED APPLICATION

This application is a continuation of application Ser. No. 08/045,369, filed Apr. 9, 1993, (now abandoned) which is a continuation-in-part of U.S. patent application Ser. No. 7/791,878 filed on Nov. 13, 1991 by Hilal, et al. (now abandoned) which was a continuation-in-part of U.S. patent application Ser. No. 07/654,815, filed on Feb. 13, 1991 by Hilal, et al. (now abandoned) and entitled Surgical Trocar.

BACKGROUND OF THE INVENTION

1. Field of the Invention

This invention relates generally to access devices and more specifically to methods and apparatus for inhibiting further cutting of tissue upon penetration of a tissue wall.

2. Discussion of the Prior Art

Devices and procedures for providing an enlarged tubular access into a body cavity or body conduit, were first conceived when catheters became widely used for minimally invasive surgery. A catheter, which may have a diameter such as 5 French, is typically very flexible and therefore does not have the column strength necessary to puncture the skin or a vessel in order to accommodate insertion of the catheter. A method which is still the preferred procedure was developed whereby a common surgical needle is inserted through the skin and into the vessel. This needle is closely overlaid with a thin sheath or introducer, which is carried by the needle into the vessel. When the needle is removed, the introducer is left in place and provides the tubular access through which the catheter can then be inserted.

In more recent times, minimally invasive surgery has further advanced so that large body cavities such as the abdomen can be accessed through tubular devices, and the surgical procedures performed with long narrow instruments through those access devices. It is not surprising that these devices, commonly referred to as trocars, are introduced through the abdominal wall or other tissue barrier, in much the same manner as that employed by the catheter introducer systems. Thus, trocars typically include a puncturing device, commonly referred to as an obturator, and a closely spaced outer sheath or cannula. In this case the obturator may have an outside diameter such as 10 millimeters, where the cannula has a similar inside diameter. Once the cannula is in place, narrow surgical apparatus can be inserted through the cannula to perform common functions such as cutting, irrigating, aspirating, grinding, traction and removal of body parts.

While the above mentioned procedure for introducing catheters has remained satisfactory, this same procedure applied to trocars has not been effective for two primary reasons. First, the size of the required puncture is much larger than that associated with catheters. Second, the abdominal wall consists of a material having a much greater density than skin or vessel walls. The puncture required for a trocar must typically be made through muscle which provides a much higher resistance to entry. As a result of these two differences, forces as great as 40 pounds may be required to insert a trocar into a body cavity.

In order to accommodate forces of this magnitude, obturators have been formed from solid metal rods and provided with very sharp points and long cutting edges leading from the point to the outer circumference of the obturator. While this has had some effect on the force required for insertion, it has only aggravated the problem associated with the presence of organs in close proximity to the abdominal wall.

In order to avoid puncturing of these interior organs, it has been necessary to stop the forward movement of the trocar immediately upon penetration. Thus the procedure has called for a tremendous force in order to penetrate the abdominal muscle and an immediate stopping of that force at the point where there is no further resistance to forward movement. In some cases, physicians have attempted to avoid the significant forward pressure by twisting and turning the trocar. This has tended to significantly traumatize the incision.

More recently, attempts have been made to mechanically cover the sharp cutting tip and edges immediately following penetration. U.S. Pat. No. 4,654,030 discloses a sheath which is biased to move forwardly over the point of the trocar as soon as it penetrates the abdominal wall. Elaborate apparatus for biasing this sheath to the forward position have been complicated by requirements for a long throwing distance and a short throwing time.

The need has remained for an apparatus and method which can easily puncture (with a low force and providing a high degree of control) along a precise incision (providing low trauma and excellent healing characteristics) while avoiding any further cutting immediately following penetration.

SUMMARY OF THE INVENTION

These features are provided in accordance with the present invention which applies electrosurgery techniques to the formation of a puncture in a body wall, such as the abdominal wall. As before, the trocar including an obturator, is advanced substantially perpendicular to the wall of the cavity but in accordance with the present invention, an electrosurgery element such as a wire or blade is provided at the distal end of the obturator. This electrosurgery element can be operated in accordance with monopolar or bipolar techniques to cut or otherwise separate the body wall as the trocar is advanced. As used herein the term electrosurgery is deemed to include the cutting, coagulating, fulgurating and desiccating of tissue.

Of particular interest to the present invention is that critical point in time when the obturator has fully penetrated the body wall and further cutting by the obturator would function only to damage interior organs. At this point in time it is desirable to insure that interior cutting does not take place. Thus means can be provided to immediately cover the obturator tip, or to withhold power from the electrosurgery element at the tip of the obturator. In the latter case, power may be withheld by ceasing its production in an associated radio frequency (RF) generator or by diverting or otherwise stopping the flow of that power to the electrosurgery element.

The invention includes means for monitoring the environmental conditions at the tip of the trocar in order to determine when the wall has been fully penetrated. By way of example, different embodiments may monitor the force on the distal tip, the presence of pneumoperitoneum pressure, tissue continuity at the distal tip, the flow of cutting current to the electrosurgical element, and other phenomena present at the interface between the abdominal wall and the interior cavity. Using these indications of wall penetration, various mechanical, pneumatic, and electrical apparatus can be employed to insure that further cutting does not occur.

In one aspect of the invention, an RF generator produces an electrical power signal and provides that signal on a power electrode. A control circuit having a control electrode facilitates presentation of the electrical power signal to the power electrode when continuity exists between the control electrode and the power electrode. A first conductor is included in the control circuit and is switchable between the control electrode and the power electrode to activate the generator. The combination also includes an obturator having a cutting element disposed at its distal tip and responsive to the electrical power signal on the power electrode to cut tissue. A second conductor is disposed to conduct the electrical power signal from the RF generator to the cutting element. A cutoff circuit responsive to an environmental condition which exists at the time of penetration, includes switch means disposed in one of the first or second conductors for inhibiting presentation of the electrical power signal to the cutting element.

The cutoff circuit may include a sensor having characteristics for sensing an environmental condition which exists in proximity to the inner surface of the wall. The sensor is responsive to this environmental condition to provide an environmental signal which can then be acted upon to inhibit further cutting of the tissue. In a particular embodiment switch means can be included in a control circuit of the generator to inhibit further presentation of the power signal to the cutting element. The switch means may include a reset which requires manual operation to reactivate the cutting element.

The logic for sensing, detecting, deactivating and resetting various elements of the system can be implemented in a mechanical switch assembly. In this aspect of the invention a trocar system includes an obturator having a shaft with a distal tip. A cutting element disposed at the distal tip has properties for being energized to cut a tissue wall. The system includes means operable to energize the cutting element and a sensor responsive to a particular condition representative of penetration of the tissue wall to provide a cutoff signal. A logic circuit responsive to the cutoff signal inhibits further cutting by the cutting element. This logic circuit may include a switch having first and second electrodes, a plunger and a lock-out element. The lock-out element can have a first position in aligned relationship with the plunger and a lockout relationship with the first electrode, a second position permitting contact between the first and second electrode to facilitate cutting by the cutting element and a third position in lock-out relationship with the first electrode and misaligned relationship with the plunger. The plunger is operable to reset the switch by moving the lock-out element from the third position to the first position.

These and other features and advantages associated with the present invention will be more apparent with a description of the preferred embodiments of the concept and reference to the associated drawings.

DESCRIPTION OF THE DRAWINGS

FIG. 1 is a side elevation view of one embodiment of the trocar associated with this invention operatively positioned to penetrate a tissue barrier;

FIG. 2 is a top plan view of the trocar embodiment illustrated in FIG. 1;

FIG. 3 is a top plan view of the distal end of a further embodiment of the trocar;

FIG. 14 is a plan view of a mechanical embodiment of the logic circuit of FIG. 13;

FIG. 14a is a cross-section view taken along lines 14a—14a of FIG. 14;

FIG. 14b is a cross-section view taken along lines 14b—14b of FIG. 14;

FIG. 15 is a side-elevation view of the mechanical switch illustrated in FIG. 14;

FIG. 25 is a axial cross-section view illustrating the trocar in an initial state;

FIG. 26 is an axial cross-section view illustrating the trocar partially actuated;

FIG. 27 is an axial cross-section view of the trocar fully actuated to cut tissue;

FIG. 28 is an axial cross-section view of the trocar in a lockout state;

FIG. 29 is a schematic view including a single spring-biased switch;

FIG. 30 is a further embodiment including a movable handle;

FIG. 31 is a further embodiment including a movable handle and two switches;

DESCRIPTION OF THE PREFERRED EMBODIMENTS

Figure 4:
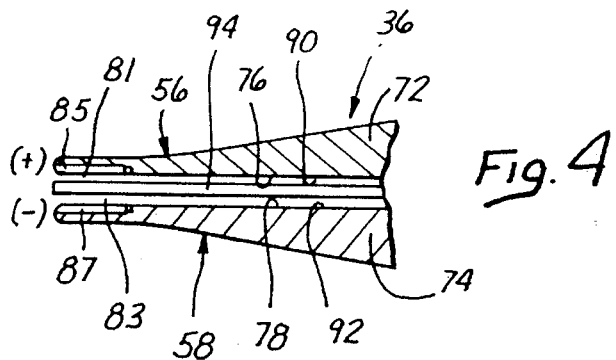
FIG. 4 is a cross-section view taken along lines 4—4 of FIG. 3.

A surgical trocar is illustrated in FIG. 1 and designated generally by the reference numeral 10. The trocar 10 is a narrow elongate instrument having a distal end 12 and a proximal end 14. It is typically configured along a longitudinal axis 16 and is generally circular in radial cross-section.

It is the purpose of the trocar 10 to provide a channel through a tissue barrier in order to provide access across the barrier into a body cavity. By way of example, an abdominal wall 18 is illustrated in FIG. 1 and typically includes a layer of skin 21, a layer of fat 23, and a layer of muscle 25 which form the tissue barrier to an abdominal cavity 27.

The trocar 10 typically includes an elongate tube or cannula 32 having a cylindrical configuration and a wall thickness such as 0.015 inches. The cannula 32 has an interior bore or channel which is typically in a range of diameters between 5 to 12 millimeters. It is the purpose of the trocar 10 to pierce, cut, incise or otherwise puncture the tissue barrier, such as the abdominal wall 18, and to leave the cannula 32 extending through that incision with a channel 34 providing an access port into the cavity 27. Through this channel 34, various surgical instruments such as cutters, clamps, traction devices, visualization devices, aspirators and irrigators can be positioned and manipulated to perform a particular surgical procedure within the cavity 27.

The trocar 10 also includes an obturator 36 which extends through the cannula 32 and provides the means for cutting through the wall 18 to provide for insertion of the cannula 32. In the past, obturators have been formed from solid metal rods which have been sharpened to a point at the distal end 12 of the trocar 10. The forces necessary to puncture the abdominal wall 18 with such a device have been considerable due primarily to the presence of the muscle layer 25 in the wall 18. Puncturing of the wall 18 with such devices has been further complicated with the close proximity of important organs such as the bowel 38 which, in some patients may actually be attached to the abdominal wall 18. In order to avoid puncturing these organs, it has been an absolute requirement that the forward movement of the trocar 10 be stopped as soon as the distal tip of the obturator pierces an inner surface 41 of the wall 18. These conflicting requirements to provide a significant puncture force and then to immediately halt application of that force, have made the trocars of the past both difficult and dangerous to use.

In accordance with the present invention an obturator 36 includes a distal tip 43 which extends beyond the distal end of the cannula 32. This tip 43 is provided with at least one cutting element, such as an electrosurgical wire 42 which can be activated through a power conductor 45 for example by an RF generator 47.

Initially the trocar 10 is advanced until the wire 42 and the tip 43 are brought into close proximity to the tissue barrier such as the wall 18. Activating the wire 42 with radiofrequency energy causes the contacted cells to vaporize forming an opening or incision in the wall 18. With the application of a relatively minimal force, the trocar 10 can be advanced through the wall 18 until the tip 43 clears the inner layer of the wall 18, such as the muscle layer 25. At this point, it is desirable to de-energize the cutting element or wire 42 so that any further forward movement of the trocar 10 does not accidently cut an interior organ such as the bowel 38. Various apparatus and methods for sensing this particular location and inhibiting further cutting are discussed in greater detail below.

At the proximal end 14 of the trocar 10, the cannula 32 is attached to a housing 50 which may include various valves of the type disclosed by Moll in U.S. Pat. No. 4,654,030, or disclosed by applicant in copending U.S. patent application Ser. No. 07/630,078 filed on Dec. 19, 1990. This housing includes a pair of finger tabs 51 discussed in greater detail below.

The obturator 36 includes an elongate shaft 52 having interior portions which define an axial channel 53 for the conductor 45. This shaft 52 extends through the housing 50 as well as the cannula 32 with the tip 43 extending beyond the distal end of the cannula 32. A handle 54, having a base plate 55, can be attached to the shaft 52 of the obturator 36 to facilitate application of the minimal axial force required to advance the trocar 10. Upon penetration of the wall 18, this handle 54 can be withdrawn to remove the shaft 52 through the cannula 32 and the housing 50. In this manner, the cannula 32 can be left in place with the interior channel 34 providing access across the abdominal wall 18 into the body cavity 27.

In the illustrated embodiment, the distal tip 43 of the obturator 36 has the configuration of a duck bill. It is defined primarily by a pair of opposing ramps 56, 58 which extend from the outer surface of the shaft 52 inwardly with progressive distal positions along the ramps 56, 68. At the distal end of the obturator 36, the ramps 56 and 58 terminate in a pair of lips 61, 63 respectively which define an interior recess 65 that is configured to receive the wire 42.

In this embodiment the lips 61, 63 extend slightly distally of the wire 42 by a particular distance. As the trocar 10 is moved forwardly, these lips 61, 63 are the only part of the trocar 10 which are intended to touch the wall 18. This particular distance is carefully selected, however, so that when the lips 61, 63 touch the wall 18, the wire 42 is close enough to the wall 18 that the most proximate cells of the tissue vaporize to create the desired incision. This cutting by close proximity is commonly referred to as arcing. As used herein the cutting element, such as the wire 42, is deemed to be in contact with the wall 18 if the desired arcing or cutting occurs.

In the embodiment of FIG. 1, the electrosurgery technique is monopolar; that is, only a single pole, such as the positive pole, is carried by the trocar 10. In this type of technique, the patient is laid directly on a large plate or grounding pad 67 which provides the second pole required by the electrosurgery system. The RF generator 47 produces a radio frequency electrical energy signal which travels through the positive electrode connected to the wire 42 and through the body of the patient, to the negative pole at the pad 67. Where this conduction path is large in cross-section, the current density is very small. However, in proximity to the wire 42 the current path is very small in cross-section so the current density is quite large. It is this large current density which results in vaporizing the cells of the wall 18 in proximity to the wire 42.

It will be apparent that a bipolar electrosurgery technique is equally applicable to this invention and may actually be preferred in some circumstances. A bipolar embodiment is illustrated in FIGS. 3 and 4 wherein the shaft 52 of the obturator 36 is separated axially into two half-shafts 72 and 74 each having in axial cross-section the shape of a half circle and each including one of the duck bills associated with the tip 43. Each of the half-shafts 72, 74 has an inner surface which defines a recess near the associated lip 61, 63 respectively. For example, the half-shaft 72 includes an inner surface 76 which defines a recess 81 near the lip 61. Similarly, the half-shaft 74 has an inner surface 78 which defines a recess 83 near the lip 63.

These recesses 81 and 83 are configured to receive a pair of blades 85, 87 respectively which are connected to the two electrical poles of the RF generator 47. Thus, the blade 85 is connected through a conductor 90 to the positive pole of the generator 47 while the blade 87 is connected through a conductor 92 to the negative pole of the generator 47. A layer of insulation 94 is sandwiched between the surfaces 76, 78 to separate the blades 85, 87. In this bipolar embodiment, current travels from the blade 85 through the tissue wall 18, around the insulation 94 and into the blade 87.

The exact configuration of the cutting elements 42, 85 and 87 in these embodiments is not important as long as the desired current density can be maintained. Thus the wire 42 and the blades 85 and 87 may be interchangeable in the FIG. 1 and FIG. 2 embodiments.

Figure 5:
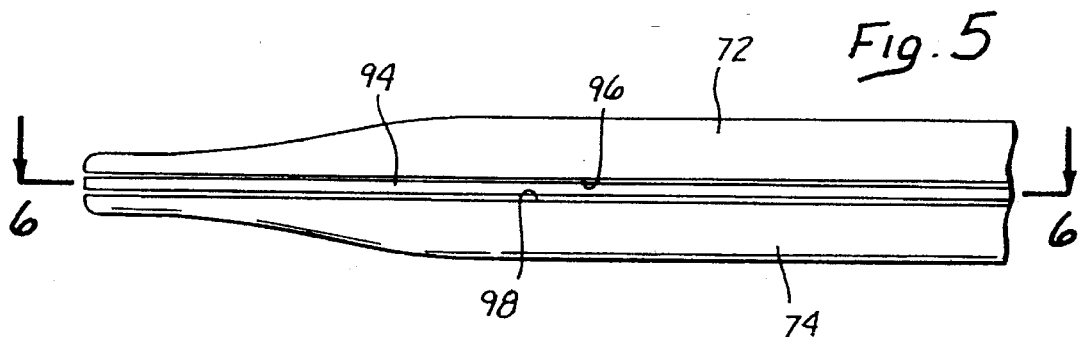
FIG. 5 is a side-elevation view of a further embodiment of the invention.
Figure 6:
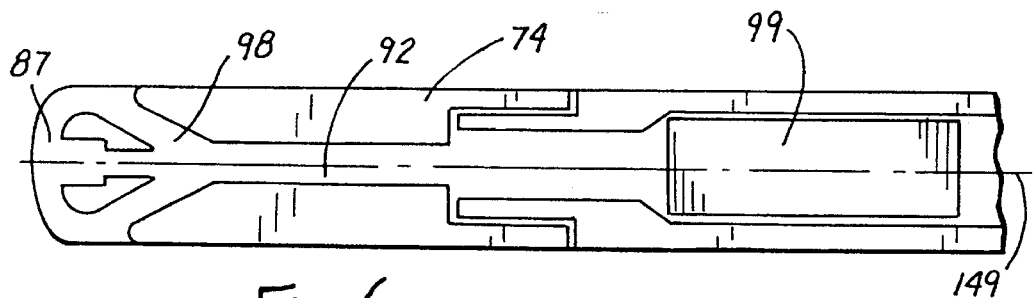
FIG. 6 is a cross-section view taken along lines 6—6 of FIG. 5.

In a further embodiment of the invention illustrated in FIGS. 5 and 6, the shaft of the obturator 36 is again separated into the half-shafts 72 and 74. Along either or both of the interior surfaces 76, 78 a conducting material can be doped into or otherwise deposited on the material forming the half-shaft 72, 74. For example, in a preferred embodiment, the half-shafts 72, 74 are formed from glass or sintered ceramic and a pair of layers 96, 98 contain a conductive polymer or metal which is doped into the surfaces 76, 78 respectively. In a monopolar embodiment, only one of the layers 96, 98 is required. In the bipolar embodiment illustrated both layers 96, 98 are required as well as the insulation layer 94 which separates the two half-shafts 72, 74.

In this particular embodiment, the doped layer, for example the layer 98, can form both the cutting element, such as the blade 87, as well as the associated conductor, such as the conductor 92. The layer 98 may also include a region of epitaxial layering which forms a logic circuit 99 discussed in greater detail below.

Figure 7:
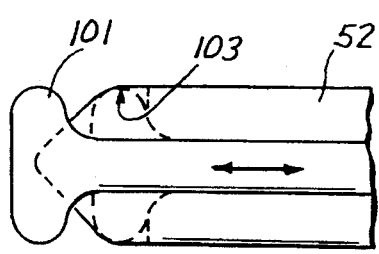
FIG. 7 is a top plan view of a further embodiment of a trocar with a retractable cutting element.
Figure 8:
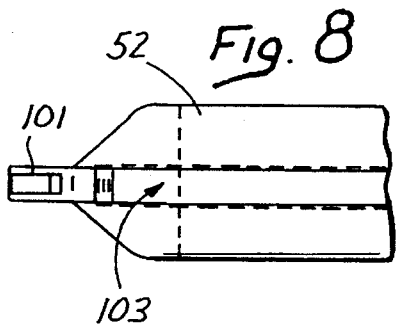
FIG. 8 is a side elevation view of the embodiment illustrated in FIG. 5.

In the embodiment of FIGS. 7 and 8, the cutting element has the configuration of a blade 101 similar to that first discussed with reference to FIG. 3. In this case, the blade 101 can be advanced beyond the distal end of the shaft 52 associated with the obturator 36. It can also be retracted into a recess 103 in the shaft 52 in order to inhibit any further cutting of the tissue associated with the wall 18. This embodiment may be of particular interest to the present invention as it provides a mechanism for controlling cutting even when the blade 101 is maintained in an energized state. Thus the cutting can occur when the blade 101 is deployed but cutting would cease when the blade 101 is retracted into the recess 103 where it is isolated from the tissue of the wall 18.

Figure 9:
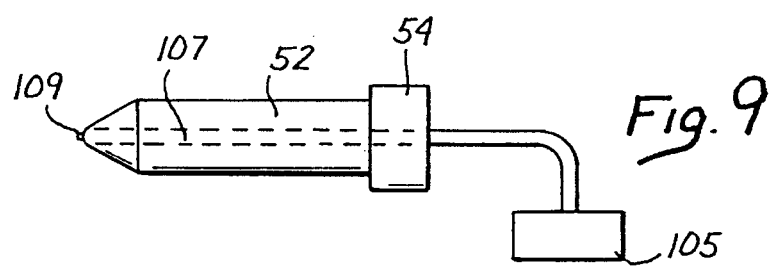
FIG. 9 is a schematic view of a trocar using an optical cutting system including a laser.

The invention is not limited to the electrosurgery embodiments or techniques disclosed above. Rather, other types of cutting elements can be disposed at the distal end of the obturator 36 to increase the cutting capabilities of the trocar 10. One such embodiment is illustrated in FIG. 9 which provides for optical cutting in combination with a laser 105. The optical energy provided by the laser 105 is conducted through an optical fiber 107 to a cutting element or lens 109 which concentrates the energy to form the required incision in the wall 18.

It will be apparent to those skilled in the art that ultrasonic cutting is equally applicable to the present invention. In such a device, the conductor would transmit energy not in the radiofrequency range but rather in the ultrasonic range between 100 KHz and 1.2 MHz. As this energy emanates from the cutting element at the distal end of the trocar 10, the energy can be focused by suitable waveguides to activate the proximate cells and cause those cells to vaporize. Thus the ultrasonic cutter would function much as a microwave. One advantage of this system is that ultrasonic cutting does not require the two electrical poles associated with both monopolar and bipolar radiofrequency cutting.

One of the most significant problems confronting trocar procedures of the past has been associated with the need to compromise two conflicting requirements: 1) the requirement to provide a significant axial pressure to force the trocar 10 through the wall 18; and 2) the need to immediately cease application of that significant force upon penetration of the wall 18. Attempts have been made to address this problem automatically and mechanically with the provision of a protective sheath armed in a rearward position but bias to spring to a distal position covering the distal tip of the obturator 36 upon penetration of the wall 18.

This attempt to avoid relying totally on the surgeon for both of the conflicting requirements has met with only limited success. Since the protective sheath has necessarily been larger than the diameter of the obturator 36, the distal end 12 of the trocar has been required to move beyond the point of penetration in order to clear the distal end of the shield. In an attempt to provide reduced insertion forces, the angle of the point at the distal end of the mechanical obturator has been reduced. While this has decreased the required insertion forces, it is also extended the length of the point 116 rearwardly along the shaft 52. This has necessarily required that the protective sheath be thrown a greater distance in order to cover the point 118 of the mechanical obturator. The critical timing of this sheath response has not been sufficient to avoid the dramatic consequences associated with interior cutting.

It is of particular importance that any cutting of tissue be restricted solely to the wall 18. Once the interior surface of the wall 18 is penetrated, any further cutting could damage interior organs, such as the bowel 38, with disastrous consequences. Sensing complete penetration of the wall can be achieved in many different ways. Of interest is any environmental condition or circumstance which exists or comes into existence when the cutting element, such as the wire 42, is in proximity to the inner surface of the wall 18. This might be a static condition which exists at all times, or a dynamic condition which first comes into existence as the distal tip 43 approaches the inner surface 41 of the wall 18.

Static conditions which are present at all times through the procedure might include the transition from tissue to the absence of tissue. Another static condition might be the presence of pressurized insufflation gasses within the cavity 27.

Dynamic conditions which could be sensed at the interior surface 41 of the wall 18 might include the penetration force associated with forcing the trocar 10 through the wall. This is the force of the wall 18 on the distal end 12 of the trocar 10, a force which ceases to exist when the distal tip 43 passes beyond the interior surface 41 of the wall 18.

Any of these static or dynamic environmental conditions could be sensed and acted upon to prevent cutting interiorly of the wall 18. For example, in a strictly mechanical trocar it is known that the absence of the dynamic force can be relied on to project a sheath over the trocar tip or to retract the tip into a sheath so that the tip is no longer exposed to cut interior organs. It will be apparent that other environmental conditions can also be sensed to accomplish the same purpose even in a mechanical trocar.

In spite of these applications to mechanical trocars, it will be apparent that the present invention provides its greatest advantages to those trocars having cutting elements which have properties for cutting tissue only when energy is produced and distributed to the cutting element. As noted this can take the form or either electrical, optical or ultrasonic energy which is first produced by a generator, such as the generator 47, and then communicated to the cutting element along an energy conductor such as the power conductor 45. In any of these systems, it is the purpose of the present invention to apply energy to the cutting element while the wall 18 is being penetrated, and to withhold energy from the cutting element when the distal end 12 is in proximity to the inner surface 41 of the wall 18.

There are several ways to insure that the energy is not applied to the cutting element. For example, the energy generator, such as the RF generator 47, could be effectively turned off so that the energy is no longer produced. Alternatively, the energy generator could be allowed to continue generating the energy but that energy would be diverted from the cutting element, such as the wire 42. Thus a switch might be placed along the power conductor 45 to stop the flow of energy to the cutting element or alternatively to divert the energy from the cutting element.

Figure 10:
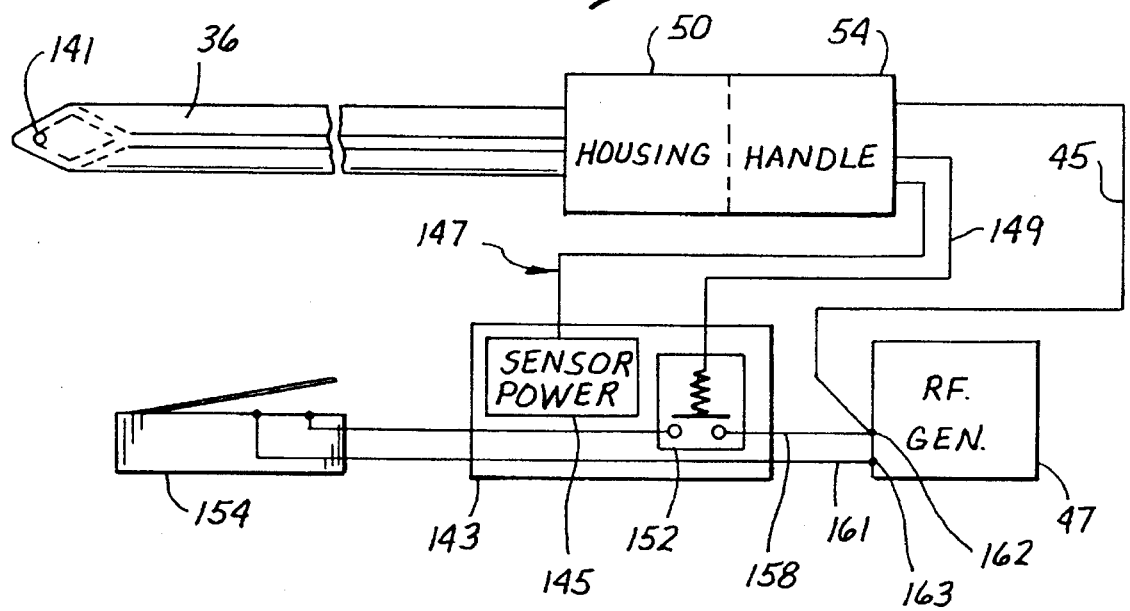
FIG. 10 is a schematic view of a preferred embodiment for sensing penetration of the tissue barrier.

With reference to FIG. 10, a particular embodiment of the obturator 36 may include means disposed near the distal end 12 of the trocar 10 for sensing penetration of the wall 18 by the obturator 36. This sensing means, represented by a sensor 141, will typically be connected to a penetration detection and response circuit 143 which controls the RF generator 47 through a pair of conductors 158, 161. In the illustrated embodiment, the circuit 143 includes a power source 145 for energizing the sensor 141 through one or more conductors 147.

By way of example, the RF generator 47 of the present invention can be that manufactured by Valleylab, Inc. and sold under the trademark FORCE 2. This generator includes a power electrode 162 and a control electrode 163 which are connected respectively to the conductors 158 and 161. Power is generated and output on the power electrode 162 only when the control electrode 163 is in contact with the power electrode 162. When continuity exists between the electrodes 162 and 163, power is output on the energy conductor 45 which conveys the power to the cutting element, such as the wire 42. When the wire 42 is energized, cutting of the tissue begins with the accompanying penetration of the wall 18.

Upon penetration of the wall 18, the sensor 141 provides an environmental signal on a conductor 149. In a particular embodiment, a switch 152 can be included in the response circuit 143 and provided with characteristics responsive to the signal on the conductor 149 to deactivate the generator 47. Thus the switch 152 may be provided with characteristics for closing when the sensor 141 is in proximity to the tissue and for automatically opening when the sensor 141 detects full penetration of the wall 18. This switch 152 can be interposed in series with a foot pedal 154 which includes a manual switch 156 for providing continuity between the two conductors 158, 161 which activate the generator 47.

With the switches 152 and 156 connected in series along the conductors 158 and 161, the opening of either the automatic switch 152 or the manual switch 156 functions to deactivate the generator 47 so that the power signal either is not produced, or the output is withheld from the power electrode 162.

Figure 11:
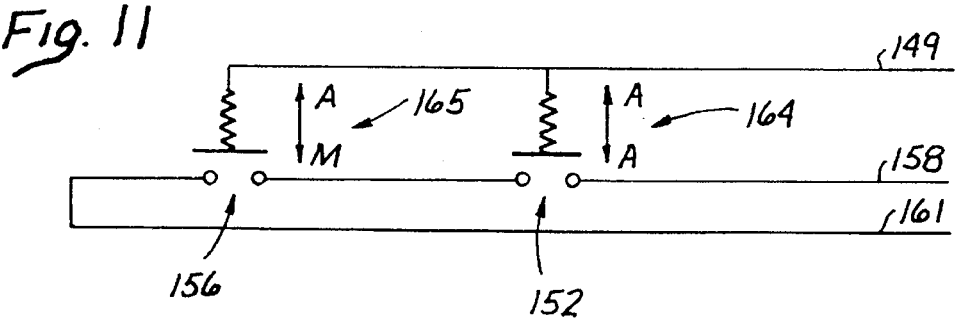
FIG. 11 is a schematic view of a switch system including an automatic switch and a manual switch.

Under certain circumstances, it may be possible that the sensor 141 would detect the absence of force on the obturator 36 merely because the physician discontinued forward movement of the trocar 10. This detection would result in the automatic opening of this switch 152 to inhibit the generator 47. Under these circumstances, the physician might decide to proceed with further cutting and therefore desire that the RF generator 47 be reactivated. This can be easily accomplished by the circuit 143 which is responsive to further pressure on the sensor 141 to close the switch 152. However, in a particular embodiment, it may be desirable to provide lock-out characteristics which require some manual switching, perhaps with the foot pedal 154, in order to reactivate the generator 47. Such a circuit is illustrated schematically in FIG. 11 wherein the switches 152 and 156 are both responsive to the signal characteristics on conductor 149 to automatically open when the sensor 141 indicates that the wall 18 has been penetrated.

If additional pressure is detected by the sensor 141, the switch 152 would automatically close as illustrated by the arrow 164. However, the switch 156 would require manual closure by the physician as illustrated by the arrow 165.

In other embodiments, the sensor 141 could be responsive to the pressure of insufflation gasses which are commonly used to inflate the abdominal cavity 27. These gases would be sensed only on the interior side of the wall 18 so the sensor 141 would actually be detecting penetration of the wall 18 by the obturator 36.

Figure 12:
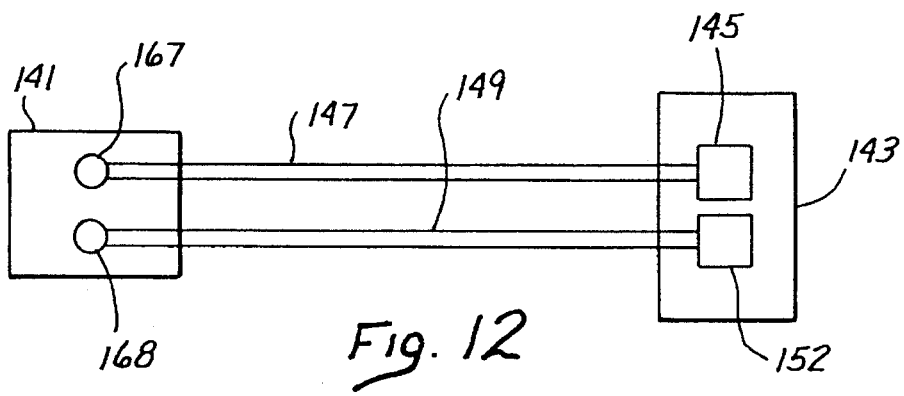
FIG. 12 is a schematic view of an infrared system for detecting penetration of the tissue barrier.

In still a further embodiment, the sensor 141 could be an infrared sensor including an LED 167 activated by the energizer 145 and a detector 168 providing the switch 152 with signal characteristics on the conductor 149. Such an IR sensor 141, as illustrated in FIG. 12, would sense the proximity of tissue by the reflectance of light from the LED 167 to the detector 168. The IR sensor 141 could also be relied on to detect the light or IR emissions of the heated electrosurgery element at the distal tip 43.

Another way of sensing penetration of the wall 18 is particularly adapted for the embodiment illustrated in FIGS. 5 and 6. In this case, the logic circuit 99 provides means for sensing changing electrical characteristics in proximity to the cutting element, such as the blade 87. These electrical characteristics may include capacitance, resistance, current magnitude, current density, or any combination thereof. These characteristics will tend to vary most dramatically as the blade 87 approaches the inner surface 41 of the wall 18. As the tissue surrounding the blade 87 is reduced in thickness, the resistance to current flow will rise. Not only will the magnitude of the current in conductor 92 decrease, but the density of the current passing through the tissue will tend to increase. Any one or all of these characteristics can be detected by the logic circuit 99 to provide a means for inhibiting further cutting of tissue upon complete penetration of the wall 18.

Figure 13:
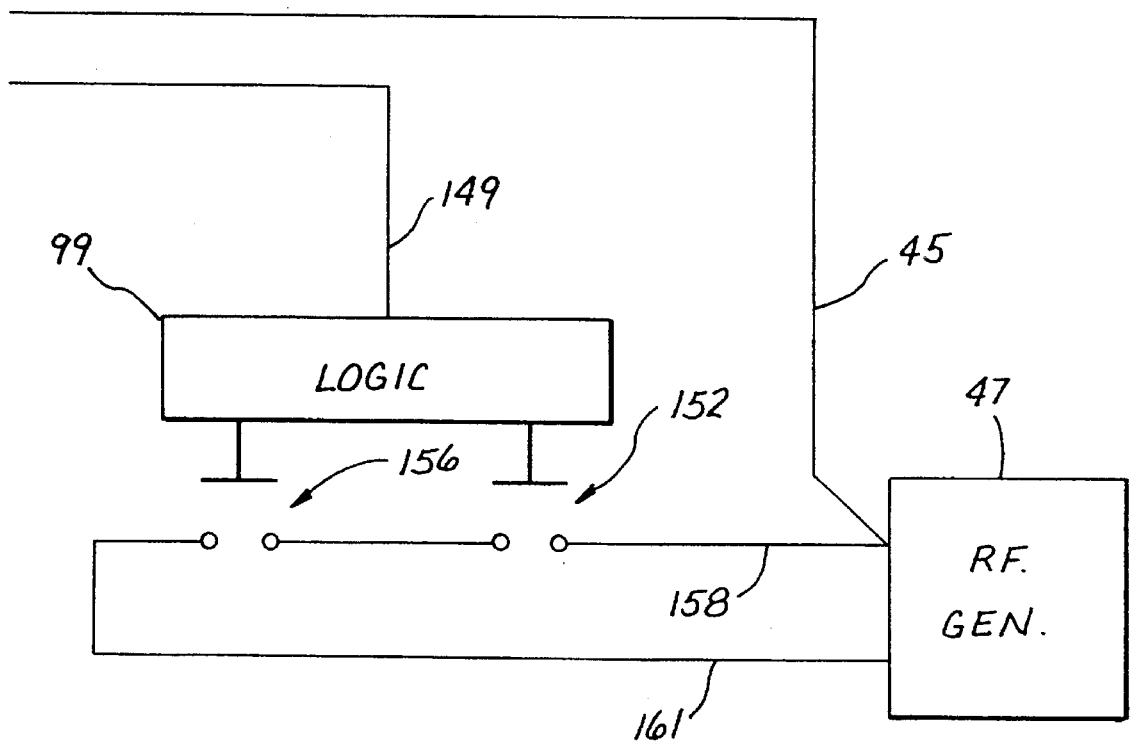
FIG. 13 is a schematic view of a further embodiment of the invention including a logic circuit.

Many other forms of logic may be implemented using the switches 152 and 156. In general, it is desirable that the switch 152 be automatically responsive to the environmental conditions which exist only at the interior surface of the wall 18. The manual switch 156 is desirable to insure that the surgeon is also ready to proceed with cutting. Logic can also be employed to provide various lock-out characteristics. In the embodiment of FIG. 13, the environmental signal from the sensor 141 is communicated to the logic circuit 99 which operates the switches 152 and 156.

Of course this logic circuit 99 can be implemented in many forms to provide a desired degree of safety. In one form of the logic circuit 99, cutting can occur only when the switches 152, 156 are both closed. If the environmental switch 152 opens, the circuit can be reactivated only if the manual switch 156 is opened and then reclosed. Thus the manual switch 156 functions as a reset for the automatic environmental switch 152.

In another form of the logic circuit 99, the switch 156 has both automatic characteristics and manual reset characteristics. This type of logic can be implemented in various forms such as the mechanical form illustrated in FIGS. 14–21. In this particular embodiment, illustrated in the side view of FIG. 15, the trocar 10 includes the cannula 32, the housing 50 with a proximally facing shoulder 172, and a pair of finger tabs which may be formed as part of the housing 50.

The associated obturator 36 includes an obturator shaft 174 which extends distally from the handle 54. This particular obturator 36 includes a conductor column 176 which extends distally into electrical contact with the electrosurgical wire 42. At the proximal end of the column 176 a cutoff and reset mechanism 180 is located within the handle 54. In a preferred embodiment of the mechanism 180, a switch terminal block 181 provides a first electrical contact. A second electrical contact is provided in the form of a switch plate 183 which is energized through the conductor 45. These two switch contacts, the terminal block 181 and the switch plate 183, form the environmental switch 156 which is of particular interest to this embodiment.

At the distal tip 43, a tip member 185 carries the electrosurgical wire 42 and is spring biased to an extended position by a compression spring 186 which is disposed between the handle 54 and the switch block 181. The spring 186 is centered on a conical projection 187 which extends from the switch block 181. The compression spring 186 functions to bias the terminal block 181, the column 176, the tip member 185 and the electrosurgical wire 42 toward a distal position relative to the handle 54. When the trocar is initially pressed against the wall 18, this tip section 185 tends to move against the bias of the spring 191, forcing the wire 42, the associated column 176, and the switch block 181 proximally relative to the obturator shaft 174. The switch block 181 also includes a flange 188 discussed in greater detail below.

The logic structure in this mechanical embodiment also includes an actuator 190 which is carried by the handle 54 and is biased by a spring 191 to a distal position where the actuator 190 contacts the shoulder 172 of the housing 50. The actuator 190 includes an extension 192 having a camming surface 194 best illustrated in FIG. 14a.

Of particular interest to the present invention is a lockout element 201 which has a longitudinal configuration and is mounted on a post 203 that is fixed to the handle 54. An elongate slot 205 is formed along the length of the element 201 to receive the post 203. This slot 205 enables the element 201 to move longitudinally relative to the post 203 and angularly around the post 203.

The lockout element 201 also includes an elbow 206 and a tang 208. A tension spring 207 is connected to the handle 54 at one end, bent around the elbow 206, and connected to the tang 208 at its opposite end. This spring 207 has two functions. First, its tension tends to bias the lockout element 201 toward the actuator 190. Second, the spring 207 produces a lateral force on the elbow 206 which tends to pivot the lockout element 201 against the actuator 190.

At the end of the element 201 opposite the slot 205, a camming surface 209 is complementary to the camming surface 194 of the actuator 190, as best illustrated in FIG. 14a. The lockout element 201 also includes a lateral camming surface 211 which moves relative to the flange 188 of the switch block 181 as best illustrated in FIG. 14b. A clearance shoulder 210 (FIG. 14), which also characterizes the lockout element 201, is also movable relative to the flange 188 on the switch block 181.

Operation of the mechanical logic circuit of this embodiment is progressively illustrated in the plan views of FIGS. 14, 16, 18 and 20 and the associated elevation views of FIGS. 15, 17, 19 and 21.

In order to energize the obturator 36 and commence cutting at the distal tip 43, the switch 156 must be closed. This is achieved when the switch block 181 moves into contact with the switch plate 183 as previously mentioned. But this contact between the switch block 181 and the switch plate 188 can happen only when certain conditions are met. Initially the obturator 36 is placed with its distal tip 43 in contact with the wall 18, and with the handle 54 disposed in the palm of the surgeon's hand. The surgeon's fingers are extended to engage the finger tabs 51 so that when the surgeon closes his hand he forces the handle 54 against the housing 50. This causes the actuator 190, which was already in contact with the shoulder 172 of the housing 50, to move proximally of the lockout element 201 which is carried by the handle 54. As this movement occurs, the surface 194 of the extension 192 on the actuator 190, cams against the surface 209 of the lockout element 201 as illustrated in FIG. 14a. This causes the element 201 to move longitudinally as the slot 205 moves relative to the post 203. Thus proximal movement of the actuator 190 and extension 192, for example along an arrow 212 in FIG. 14a, is accompanied by axial movement of the lockout element 201, for example along an arrow 214.

Figure 16:
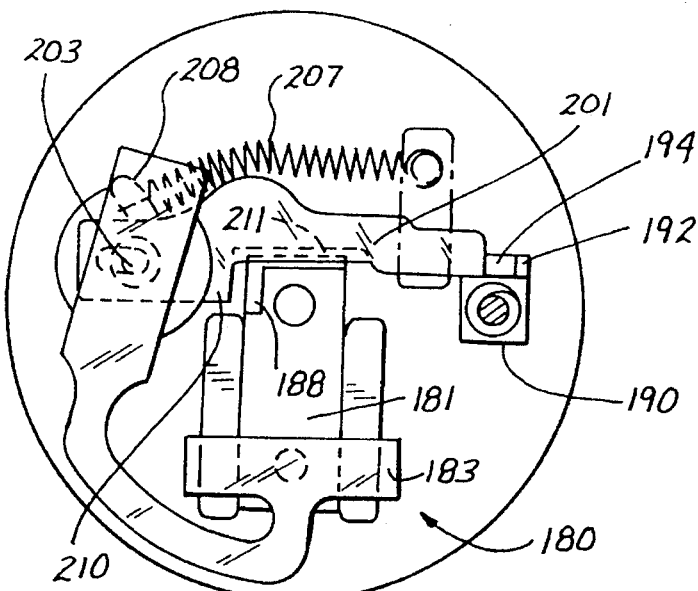
FIG. 16 is a top plan view illustrating the mechanical switch in a second position.
Figure 17:
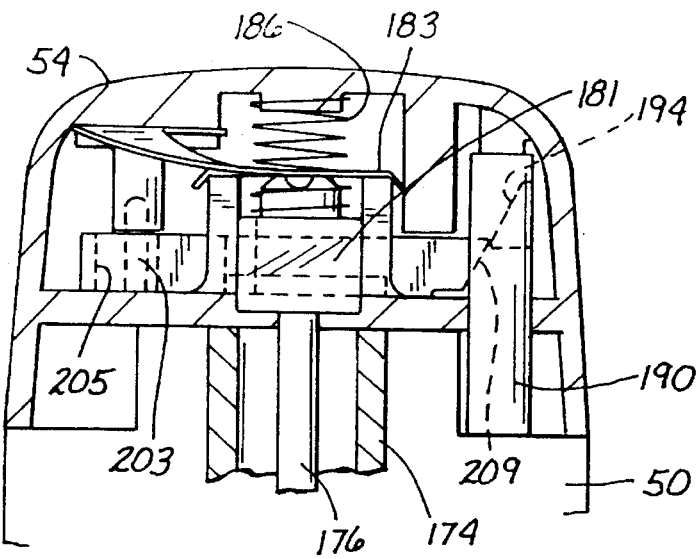
FIG. 17 is a side elevation view of the mechanical switch of FIG. 16.

When this camming action is fully completed, the post 203 is disposed at the inner end of the slot 205 and the shoulder 210 of the lockout element 201 clears the flange 188 of the switch block 181. This second position of the lockout element 201 is illustrated in FIGS. 16 and 17. In this position, the switch block 181 is free to move proximally, upwardly in FIG. 17.

Figure 18:
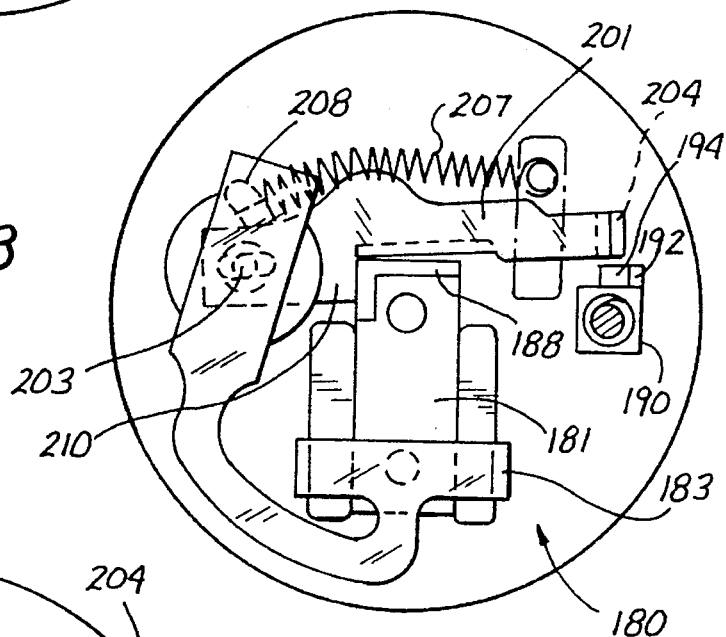
FIG. 18 is a top plan view illustrating the mechanical switch in a third position.

As the switch block 181 moves upwardly, for example in the direction of an arrow 216 in FIG. 14b, the flange 188 cams against a lateral camming surface 217 on the lockout element 201. This tends to move the lockout element 201 laterally, for example in the direction of an arrow 218. This lateral movement of the lockout element 201 is accommodated by rotation of the element 201 about the post 203 and against the bias of the spring 207. This bias also tends to move the element 201 longitudinally until the shoulder 210 contacts the edge of the flange 188, as illustrated in FIG. 18.

Figure 19:
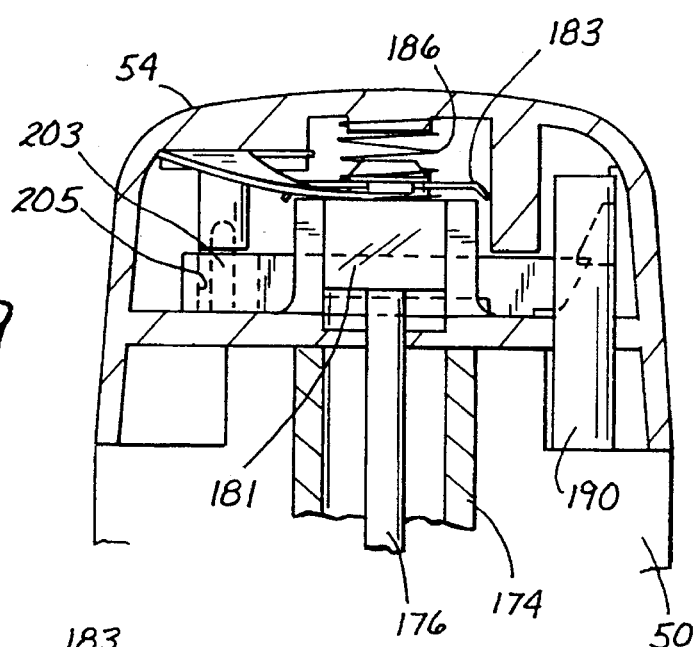
FIG. 19 is a side elevation view of the switch illustrated in FIG. 17.
Figure 21:
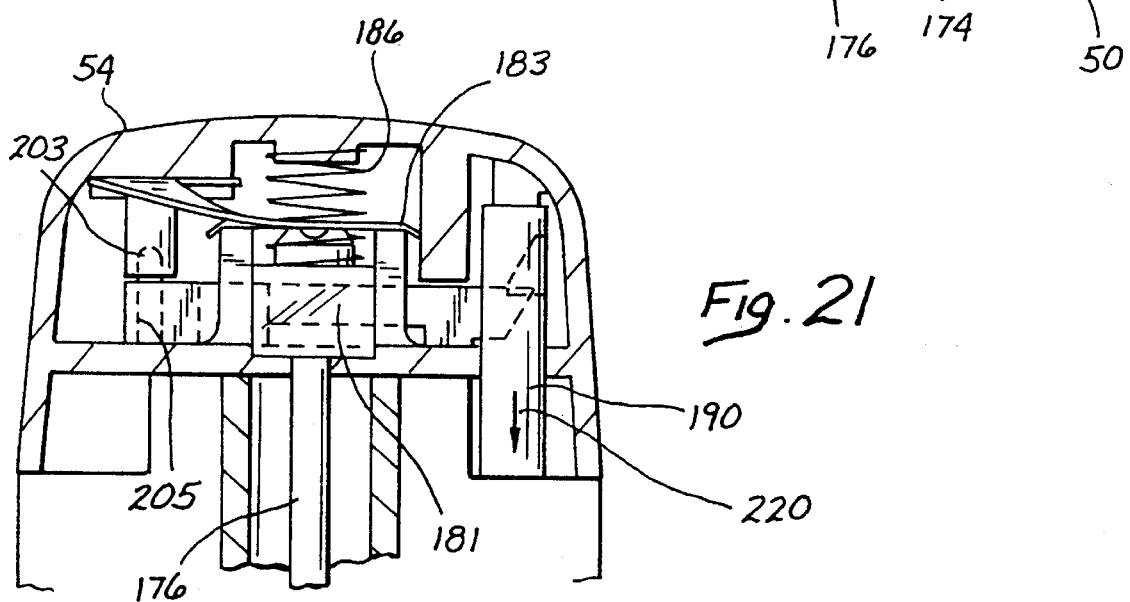
FIG. 21 is a side elevation view of the switch of FIG. 20.

When the flange 188 clears the surface 217 of the lockout element 201, the switch block 181 is free to move into engagement with the switch plate 183 to close the switch 152 and permit cutting at the distal tip 43. This third position of the lockout element 201 is illustrated in FIGS. 18 and 19 where it is important to note that the end of the element 201 including the camming surface 217 has moved longitudinally beyond the extension 192 of the actuator 190.

As cutting progresses, if the force on the distal tip 43 is not maintained, the compression of the axial spring 186 will immediately force the switch block 181 to disengage the switch plate 183. This of course will stop the cutting.

This absence of force on the distal tip 43 can occur in at least two ways. Importantly, if the distal tip 43 has fully penetrated the wall 18, the absence of force will result from movement of the distal tip 43 into the cavity 27. In accordance with one objective of the invention, it is important that cutting cease in this scenario in order to avoid any puncture or penetration of interior organs. The absence of a force on the distal tip 43 may also occur if the surgeon discontinues pressure on the handle 54. This may be a momentary discontinuance of force but it will have the same effect, specifically, the switch block 181 will separate from the switch plate 183 and cutting will cease. In this scenario, the lockout structure previously described will prevent further cutting even in the presence of increased pressure on the handle 54. This can be better understood by again tracking movement of the switch block 181, the element 201 and the actuator 190.

An absence of force on the distal tip 43 not only causes the switch block 181 to disengage the switch plate 183 but it also causes the block 181 to move distally, downwardly relative to the lockout element 201. This downward movement occurs until the flange 188 of the block 181 clears the shoulder 210 at which point the element 201 moves longitudinally and pivots toward the actuator 190. This brings the lockout element 201 to its fourth position best illustrated in FIG. 20 and 21.

Figure 20:
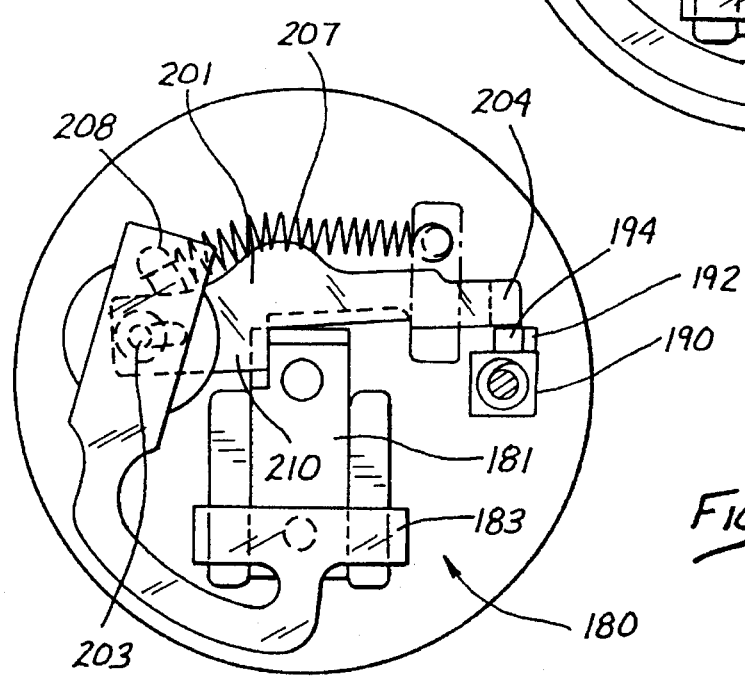
FIG. 20 is a top plan view illustrating the switch in a fourth position.

This fourth position can be reached only from the third position illustrated in FIGS. 18 and 19. But in this third position, the lockout element 201 is displaced longitudinally beyond the extension 192 so that further angular movement of the element 201 can not align the camming surfaces 194 and 209. Rather, the lockout element 201 is biased against the side of the extension 192 as shown in FIG. 20. Only when the surgeon releases the finger tabs 51 and permits the handle 54 to disengage the housing 50, is the actuator 190 free to move downwardly, for example in the direction of an arrow 220 in FIG. 21. In response to this downward movement, the lockout element 201 clears the extension 192 and the spring 207 pivots the element 201 against the actuator 190 with the extension 192 aligned beneath the camming surface 209 of the element 201. Having released the handle 54 from the housing 50, the surgeon can again squeeze these two elements into proximity forcing the camming surface 194 of the actuator 190 against the camming surface 209 of the lockout element 201 as first described with reference to FIGS. 14 and 15.

Thus, a mechanical lockout is provided which insures that once cutting starts, if it stops, an active conscience effort must be made by the surgeon to restart the cutting.

Figure 22:
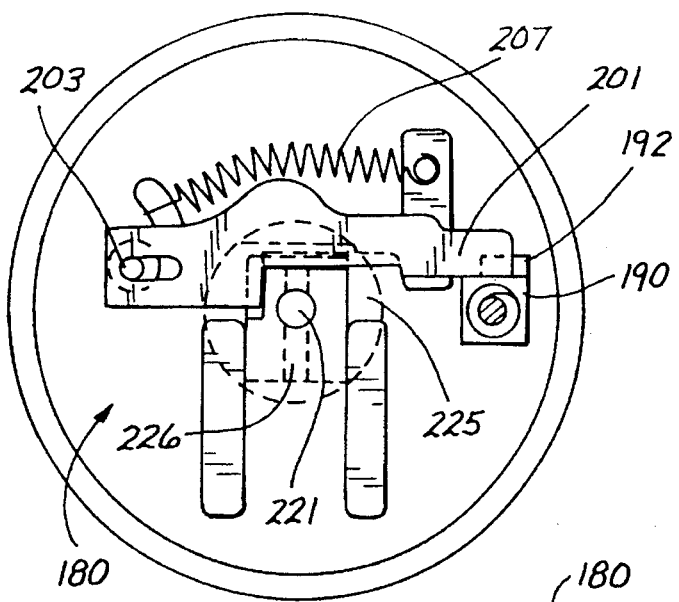
FIG. 22 is an axial cross section view of a further embodiment of the invention illustrating a mechanical logic circuit in combination with a mechanical obturator.
Figure 23:
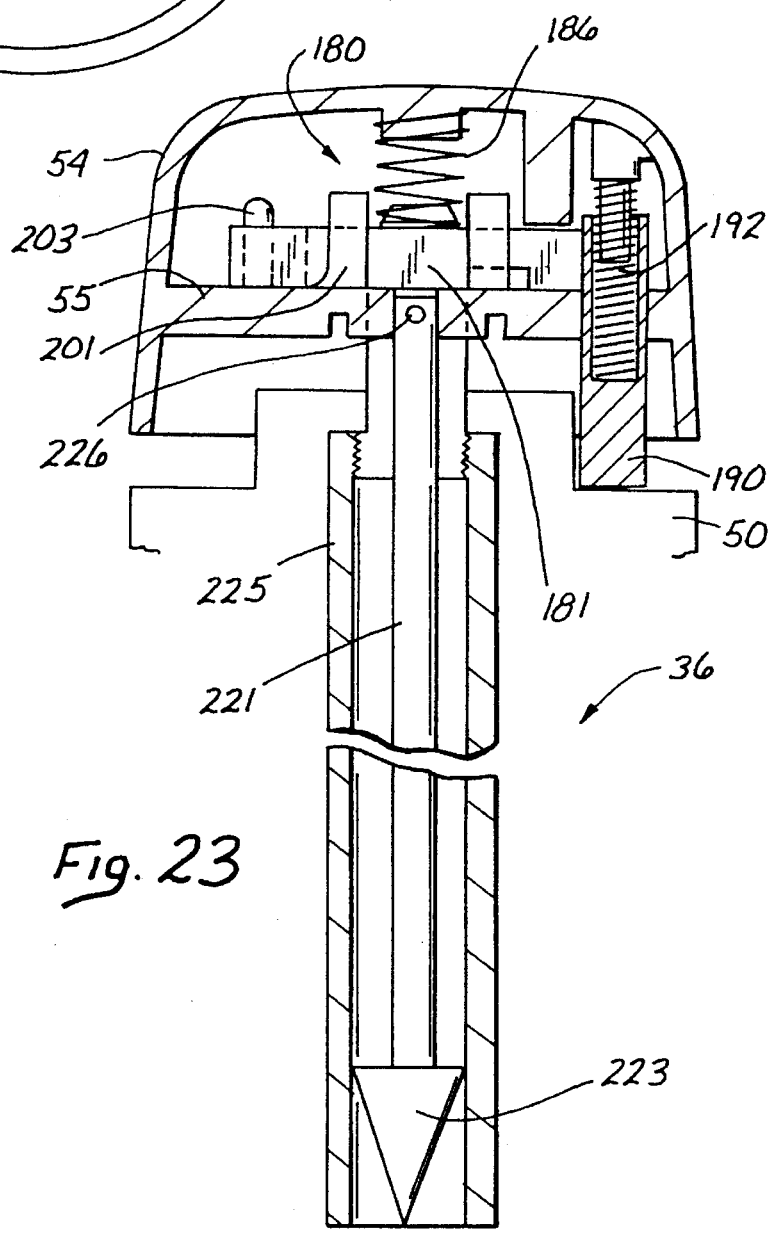
FIG. 23 is a radial cross section view taken along lines 23—23 of FIG. 22.
Figure 24:
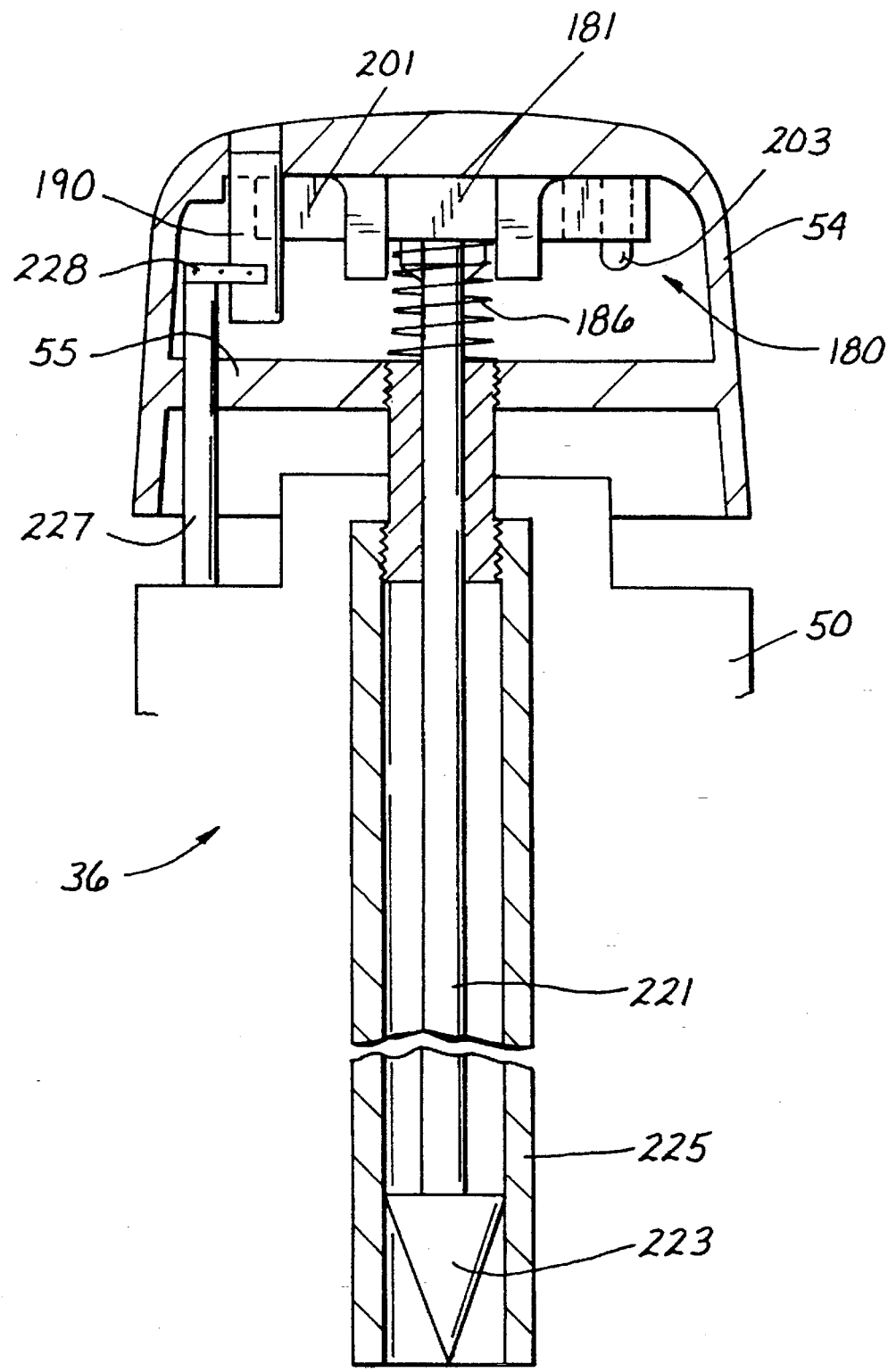
FIG. 24 is an axial cross section view of a further embodiment of the Invention similar to FIG. 22 but with the mechanical circuit inverted.

The embodiments of FIGS. 22 and 23 are similar to that of FIGS. 14 and 15 except the cutoff and reset mechanism 180 is applied to a strictly mechanical trocar. While the embodiment of FIGS. 14 and 15 required a flow of electrical current in order to energize the wire 42 at the distal tip 43, the embodiments of FIGS. 22 and 23 do not include such a wire. Rather, these embodiments include an obturator core 221 having a sharp distal tip 223 which may have the configuration of a pyramid. An outer sheath 225 surrounds the core 221 and is movable longitudinally relative to the core 221. In a first position, the sheath 225 is displaced proximally of the core 221 to expose the sharp distal tip 223. With this orientation, the sharp tip 223 can be forced through the abdominal wall 18 along with the core 221 and sheath 225. When the wall 18 has been fully penetrated, the core 221 and sheath 225 move relative to each other to a second position where the sheath 225 covers the distal tip 223 of the core 221.

This relative movement of the core 221 and sheath 225 is easily accommodated by the cutoff and reset mechanism 180 illustrated in FIGS. 14 and 15. Thus the embodiments of FIGS. 22 and 23 also include the actuator 190 having the extension 192 and the lockout element 201 which is movable relative to the post 203. The springs 186 and 207 are also included in this embodiment along with the block 181. In this case, the block 181 moves longitudinally in the manner previously described, but it does not perform the function of an electrical contact. Also, the switch plate 183 of FIG. 14 is specifically absent from this mechanical embodiment of the obturator 36.

In the embodiment of FIG. 22, the core 221 can be screwed into the base plate 55 or fixed to the base plate 55 by a pin 226. Thus the core 221 has a fixed relationship with the handle 54. The sheath 225 is fixed to the block 181 and is movable with the block 181 relative to the handle 54 and the core 221.

With this configuration, the embodiment of FIGS. 22 and 23 functions to expose the sharp distal tip 223 when cutting is desired, and function to cover the distal tip 223 with the sheath 225 when cutting is no longer desired. As noted, this function is achieved in the embodiment of FIG. 22 by attaching the core 221 to the base plate 55 and by attaching the sheath 225 to the block 181.

In this embodiment the cutoff and reset mechanism 180 functions in the manner previously described. As the handle 54 is squeezed against the housing 50, the actuator 190 moves proximally. This action causes the lockout element 201 to move laterally thereby permitting the block 181 to move proximally with the sheath 225. This proximal movement of the block 181 is accomplished against the bias of the spring 186 by an axial force on the sheath 225 at the distal tip 223. At this point, the sharp tip 223 of the core 221 is exposed and axial cutting can progress.

If the surgeon stops cutting in the middle of the abdominal wall 18 or if the obturator 36 fully penetrates the wall 18, the block 181 will move distally in the manner previously described. This will cause the sheath 225 to cover the sharp tip of the core 221 but will also cause the lockout element 201 to move into a position of misalignment with the actuator 190. In this position of misalignment, further pressure on the obturator 36 will not permit the sheath 225 and block 181 to move proximally.

This lockout condition exists until the surgeon relaxes his hand thereby permitting the handle 54 to withdraw from the housing 50. Under these conditions the actuator will move distally permitting the lockout element 201 to align with the extension 192. Once the mechanism 180 has been reset in this manner, if the surgeon desires further cutting, the handle 54 can again be brought into engagement with the housing 50 thereby permitting the sheath 225 to withdraw and expose the sharp tip 223 of the core 221.

The embodiment of FIG. 23 is similar to that of FIG. 22 except that the cutoff and reset mechanism 180 is inverted in the handle 54, and the core 221 and sheath 225 are reversed in their respective attachments to the block 181 and the base plate 55. It will also be noted that the actuator 190 is inverted so that a plunger 227 and associated pivot lever 228 are required.

In this embodiment of the obturator 36, the sheath 225 is held stationary by its attachment to the base plate 55 while the core 221 with its sharp distal tip 223 is attached to and movable with the block 181. This is accomplished with the same cutoff and reset mechanism 180 but in this particular case, the mechanism 180 is inverted and the core 221 extends through the spring 186. Otherwise, the mechanism 180 functions in the manner previously discussed.

Cutting is facilitated when the block 181 moves in the direction of the spring 186, but this direction has been reversed so that movement is now in the distal direction. This distal movement is conveyed to the core 221 which then moves beyond the stationary sheath 225 to provide the desired exposure and cutting. When cutting has been completed, the core 221 moves proximally with the block 181 by action of the compression spring 186. Thus the core 221 is withdrawn into the stationary sheath 225 to inhibit further cutting by the sharp distal tip 223.

The cutting process begins in the manner previously discussed except that movement of the handle 54 into proximity with the housing 50 pushes the plunger 227 proximally and, through the pivot lever 228, moves the actuator 190 distally. From this point, the cutoff and reset mechanism 180 functions in the manner previously discussed. From the lockout position, the mechanism 180, is reset by permitting the handle 54 to withdraw from the housing 50. This causes the actuator 190 to move proximally and, through operation of the lever 228, enables the plunger 227 to move distally thereby resetting the mechanism 180.

The logic circuit 99 of FIG. 13 can also be implemented mechanically in a further embodiment of the invention which is illustrated in FIGS. 25–28. In this embodiment, some of the elements have characteristics which are similar to those previously discussed, and consequently are designated by the same reference numeral. Thus in FIG. 28, the trocar 10 includes a cannula (not shown) and housing 50. The obturator 36 includes the handle 54 and the shaft 52 with the wire 42 disposed at the distal tip 43.

In this embodiment, the shaft 52 is movable axially relative to the handle 54, between a first position best illustrated in FIG. 25 and a second cutting position best illustrated in FIG. 27. A lockout sheath 231 is also provided exteriorly of the shaft 52. This sheath 231 is fixed to the handle 54 and moves with the handle 54 relative to the shaft 52.

A lockout element or tang 233 is carried by the sheath 231 and is movable between a first location illustrated in FIG. 25 and a second location illustrated in FIG. 28. In the first location, the tang 233 permits the shaft 52 to move freely between its first and second position. However, in the second location, the tang 233 functions to maintain the shaft 52 in its first position effectively inhibiting movement of the shaft 52 to its second, cutting position.

A reset element in the form of a ring 235 circumscribes the shaft 52 and is movable between a first disposition illustrated in FIG. 25 and a second disposition illustrated in FIG. 27. In its first disposition, the ring 235 maintains the tang 233 in its first location thereby permitting the shaft 52 to move proximally to its second, cutting position. When the ring 235 is located in its second disposition, the shaft 52 may either be in its second cutting position as illustrated in FIG. 27, or it may be in its first position and locked out from its second position by the tang 233 as illustrated in FIG. 28.

The embodiment of FIG. 25 also includes a reset sleeve 237 which is movable relative to the lockout sheath 231 and the shaft 52. This sleeve 237 extends between the sheath 231 and the shaft 52 and inside the ring 235. A shoulder 239 on the sleeve 237 permits the sleeve 237 to engage the ring 235.

The sleeve 237 extends proximally to the handle 54 where it is connected to a cross member 241 that is also connected to an actuator 243. The sleeve 237, cross member 241 and actuator 243 and movable between a first state illustrated in FIG. 25 and a second state illustrated in FIG. 26. In the first state, the handle 54 is spaced from the housing 50 and the sleeve 237 is positioned distally maintaining the ring 235 in its first disposition.

In its second state, the handle 54 is brought into proximity with the housing 50 as the surgeon squeezes these two elements together. This disposition of the handle 54 and housing 50 moves the actuator 243 into the handle 54 thereby creating an annular space 244 proximally of the ring 235 in its first disposition. The switch 156 is disposed between the cross member 241 and the handle 54. When the surgeon squeezes the handle 54 against the housing 50, the actuator 243 closes the switch 156 in the logic circuit 99 (FIG. 13). The second switch 152, is disposed between the shaft 52 and the cross member 241. This switch 152 is closed when the shaft 52 and the sleeve 237 are in their respective first position and first state. This switch 152 is also closed when the shaft 52 and sleeve 237 are in their respective second position and second state as illustrated in FIG. 27.

Two compression springs 245 and 247 are associated with the reset sleeve 237. The spring 245 is disposed between the handle 54 and the cross member 241. In this position, it biases the reset sleeve 237 to its first position as illustrated in FIG. 25. The spring 247 is disposed between the sleeve 237 and the shaft 52. In this position, the spring 247 functions to automatically move the shaft 52 to its first distal position when the sleeve 237 is in its second proximal position.

In operation, the trocar 10 is initially configured as illustrated in FIG. 25. The shaft 52 is in its first position, the tang 233 is in its first location, the ring 235 is in its first disposition, and the sleeve 237 is in its first state. Initially the surgeon squeezes the handle 54 against the housing 50 as illustrated in FIG. 26. This closes the switch 156 and opens the switch 152. This also causes the sleeve 237 to be moved proximally within the handle 54 thereby creating the space 244 between the shoulder 239 and the ring 235. As the surgeon presses the distal tip 43 of the shaft 52 against the abdominal wall 18, the ring 235 is moved through the space 244 into engagement with the shoulder 239. This pressure of the distal tip 43 against the abdominal wall also moves the shaft 52 against the cross member 241 to close the switch 152. With both the switch 152 and the switch 156 closed, as illustrated in FIG. 27, current flows along the conductor 45 to energize the wire 42 at the distal tip 43 and permit the cutting of tissue.

When pressure is no longer maintained on the distal tip 42, the spring 247 functions to separate the shaft 52 from the cross member 241 thereby opening the switch 152 so that further cutting of tissue is prevented. This absence of pressure at the distal tip can occur when the wire 42 fully penetrates the wall 18. In this case, the prevention of further cutting functions to insure that the interior organs are not damaged.

The absence of pressure at the distal tip 43 can also occur when the cutting wire 42 is in the middle of the abdominal wall 18 and the surgeon fails to maintain pressure on the handle 54. As previously discussed, under these circumstances some conscious mechanical effort on the part of the surgeon is desired in order to continue cutting.

In this particular embodiment, when the shaft 52 separates from the cross member 241, an annular space 251 develops distally of the ring 235. The tang 233 automatically falls into this space 251 and inhibits any movement of the shaft 52 from its first extended position to its second cutting position. This state of the trocar 10 is illustrated in FIG. 28. In order to continue cutting, from this point the surgeon must consciously permit the handle 54 to disengage the housing 50 as illustrated in FIG. 25. Under these conditions, the spring 245 will force the reset sleeve 237 to move from its second position to its first position. During this movement, the shoulder 239 engages the ring 235 in its second disposition and moves it distally to its first disposition as illustrated in FIG. 25. As the ring 235 moves distally, the tang 233 moves radially outwardly clearing the shaft 52. This removes the tang 233 from the space 244 so the shaft 52 is free to move to the second position as previously discussed.

The logic circuit 99 of FIG. 13 can also be implemented mechanically in embodiments illustrated in FIGS. 29–32. These embodiments rely upon the sensing of pneumoperitoneum pressure within the cavity 27 in order to open the environmental switch 152 and inhibit further cutting. These embodiments of the obturator 36 also include the obturator shaft 52 and handle 54. The conductor 45 provides cutting power from the RF generator 47 to the wire 42 at the distal tip 43. A channel 261 is formed within the shaft 52 and extends between a distal port 263 and the interior of the handle 54.

Within the handle 54, a bellows 265 communicates with the channel 261 and includes a diaphragm 267 which moves proximally when elevated pressures are present at the distal port 263. Also included within the handle 54 is a switch contact 270 which is associated with the switch 152 and biased against the handle 54 by a compression spring 272. In its normal position, the switch contact 270 is held against the diaphragm 267 of the bellows 265 in electrical contacting relationship with a pair of electrodes 274 in the conductor 45.

As long as these conditions exist, the obturator 36 is powered by the generator 47 to cut the abdominal wall 18. When the wall 18 is fully penetrated, the distal tip 43 of the obturator 36 extends beyond the wall 18 into the abdominal cavity 27. Insufflation gasses in the cavity 27 are immediately encountered at the distal port 263 and communicated through the channel 261 to the bellows 265. In response to this elevated pressure, the bellows 265 expand forcing the diaphragm 267 proximally and elevating the switch contact 270 from the electrodes 274 against the bias of the spring 272. When the electrodes 274 are no longer in contact, power through the conductor 45 is inhibited so no further cutting can occur. In this embodiment, the switch contact 270 is operable under the single influence of the environmental conditions present at the distal port 263.

The embodiment of FIG. 30 is similar to that of FIG. 29 except that the switch 152 is operable not only in response to the environmental conditions but also in response to input from the surgeon. In this embodiment, the handle 54 floats axially within a handle enclosure 281. A compression spring 283 biases the handle 54 from the sides of the bellows 265 to a proximal position. Since the switch contact 270 is attached to the handle 54 by the spring 272, this proximal position also holds the switch contact 270 from electrical engagement of the electrodes 274. In this embodiment, the handle 54 must be depressed by the doctor against the force of the spring 272 to move the switch contact 270 into engagement with the electrodes 274 and the diaphragm 267.

The switch 152 will open under either of two conditions. First, if pneumoperitoneum pressure is sensed at the distal port 263, the diaphragm 267 will move the switch contact 270 from electrical engagement with the electrodes 274 to cease production of power by the RF generator 47. Also, if the surgeon ceases to press the handle 54 against the spring 272, the handle 54 will move to the proximal position removing the switch contact 270 from the electrodes 274. Under either of these conditions, power to the cutting wire 42 will be discontinued.

Similar functions can be embodied in the obturator 36 illustrated in FIG. 31. This embodiment is similar to that illustrated in FIG. 30 except that the switch contact 270 is normally closed and is not influenced by the position of the handle 54. In this embodiment, the second switch 156 is provided in the conductor 158, in series with the environmental switch 152. This switch 156 is closed in response to the surgeon's pressure on the handle 54 and is automatically opened by the spring 272 when this pressure is removed.

Figure 32:
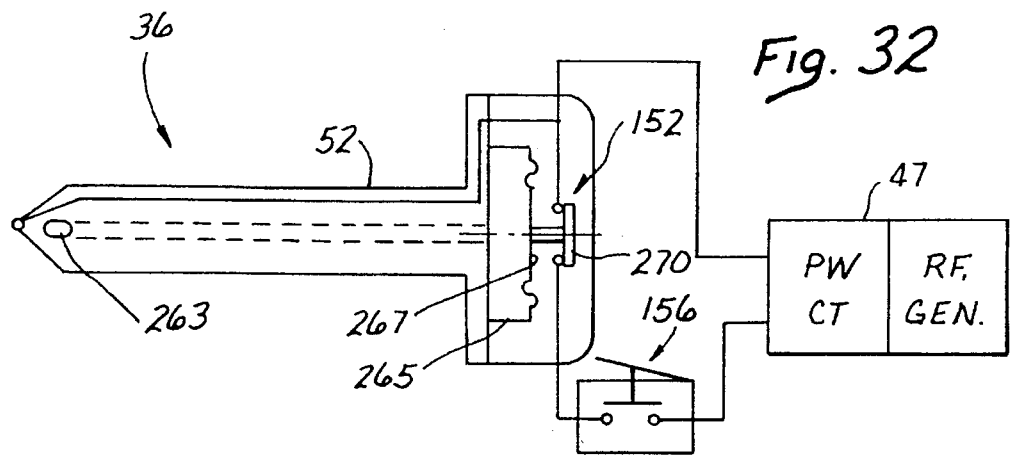
FIG. 32 is a further embodiment including a foot switch.

A further embodiment illustrated in FIG. 32 is similar to that of FIG. 29 in that the handle 54 is not movable with respect to the shaft 52 of the obturator 36. It is similar to the embodiment of FIG. 31 in that the switch 152 is normally closed in the absence of a spring 272. The embodiment of FIG. 32 also includes the second switch 156 but this switch is embodied in the form of a foot pedal which is external to the obturator 36.

Figure 33:
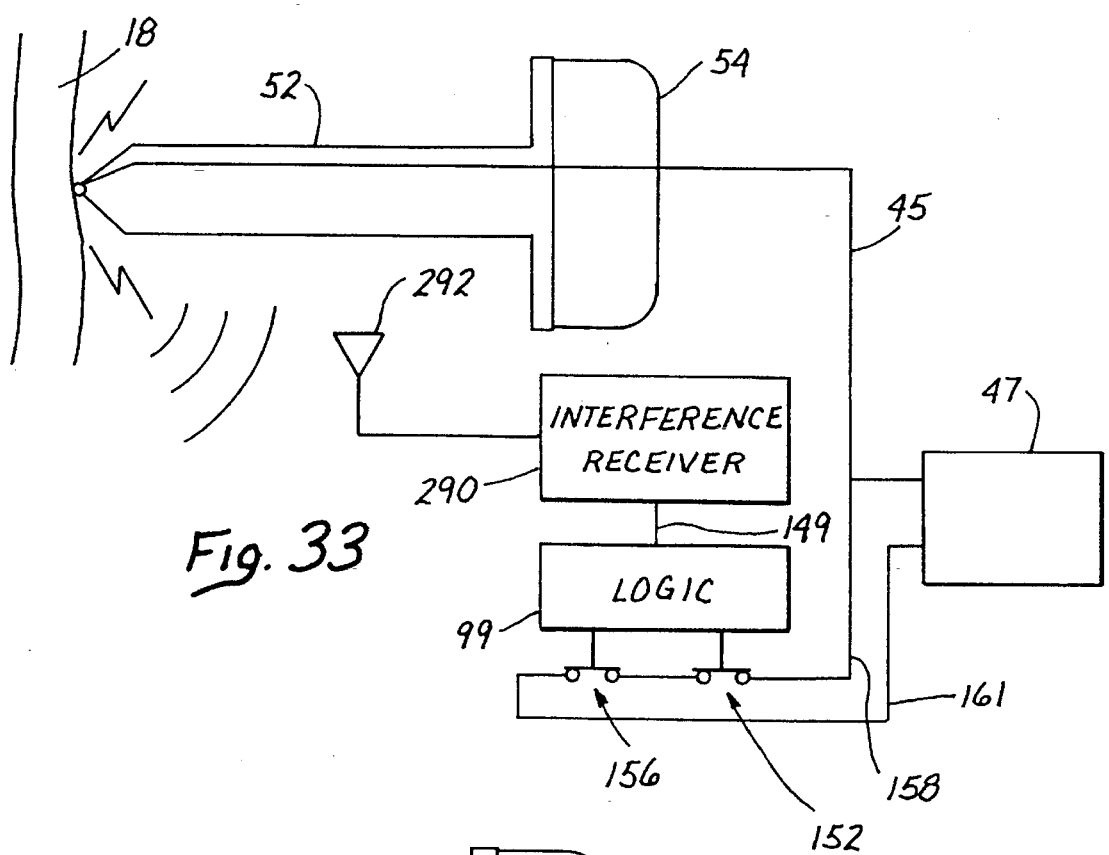
FIG. 33 is a further embodiment of the invention including an interference receiver for activating the cutoff circuit.

As previously noted, each of the embodiments in FIGS. 29–32 rely upon the sensing of pneumoperitoneum pressure within the cavity 27 in order to discontinue cutting by the obturator 36. Other phenomena present at the interior surface of the wall 18 can also be relied upon to discontinue cutting by the obturator 36. In the embodiment of FIG. 33, the obturator 36 is similar to that previously discussed with reference to FIG. 16 except there is no separate connection, for example along the conductor 149, between the sensor 141 and the logic circuit 99. This embodiment relies upon the phenomena which occurs when the cutting of tissue is taking place. This cutting of tissue generates interference noise in a range of frequencies between 5 and 17 kilohertz. This noise may also be detectable in a range of harmonic frequencies such as 80 and 108 megahertz.

Relying upon the presence of these interference frequencies during cutting, the embodiment of FIG. 33 includes an interference receiver 290 having an antenna 292. As cutting progresses, the interference signal is received by the antenna 292 and detected by the receiver 290 which provides an environmental signal on the conductor 149 to the logic circuit 99. In this embodiment, the environmental switch 152 would initially be closed to enable cutting to start. Once cutting started and the interference signal was present on the conductor 149, the logic circuit 99 would control the switch 156. When the interference signal was no longer present on the conductor 149 as would be the case when cutting was completed, the logic circuit 99 would automatically open the environmental switch 152 and discontinue further cutting by the obturator 36.

Figure 34:
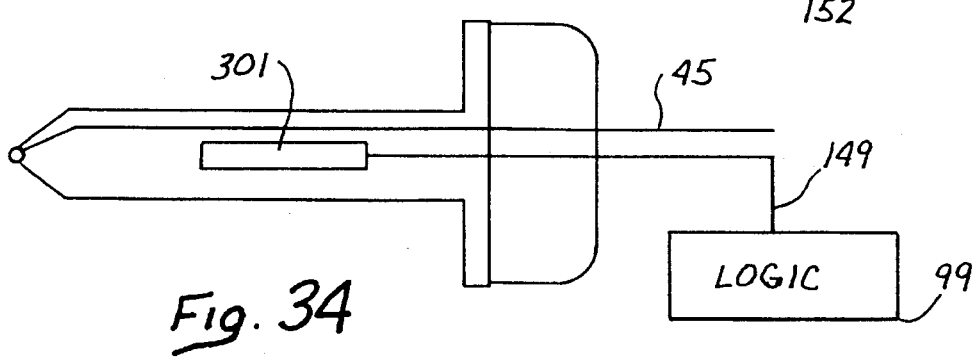
FIG. 34 is a further embodiment including a Hall-effect transistor for activating the logic circuit of the present invention.

Other phenomena associated with the actual cutting of the tissue can be relied upon to stop the cutting when the wall 18 is fully penetrated. In the embodiment of FIG. 34 a Hall-effect sensor/transistor 301 is provided in close proximity to the power conductor 45. This proximity could be provided within the shaft 52, the handle 54, or anywhere along the power conductor 45 between the generator 47 and the obturator 36. The Hall-effect sensor/transistor 301 has properties for determining whether current is flowing along the power conductor 45. As long as this current is flowing, the output of the transistor would provide an environmental signal, for example on the conductor 149, to the logic circuit 99. When current flow on the conductor 45 ceases indicating that the tissue of wall 18 is being cut, the signal on the conductor 149 will change providing an indication to the logic circuit 99 that no further cutting is to be permitted. In the manners previously discussed, the logic circuit 99 would either inhibit further production of the power signal or otherwise discontinue cutting at the distal tip 43. Other known methods and sensors for detecting the flow of a current along a conductor, such as the power conductor 45, could also be implemented in this embodiment of the invention.

The foregoing embodiments are just a few of those which rely upon a cutoff circuit, either electrical or mechanical to cease cutting by the obturator 36 upon penetration of the wall 18. A requirement of each of these embodiments is that some condition be sensed which is in existence only at the inner surface 41 or which first comes into existence when the distal tip 43 moves into proximity with the inner surface 41. This condition may be inherent in the force required for forward movement of the obturator or it may be a condition sensed for example by the sensor 141. The sensed condition can be implemented in a mechanical, electrical, ultrasonic or optical obturator. For example, in a mechanical obturator, the cutoff signal from the sensor 144 can be used to activate a solenoid for moving the obturator shaft 52 relative to a protective sheath.

Many alternatives are available in the case of an electrosurgical trocar. In such an instrument, the sensed condition can be implemented in a mechanical cutoff circuit or an electrical cutoff circuit. The electrical circuit can cease production of the power signal or divert or otherwise inhibit the power signal in response to the sensed condition. Such a circuit can be implemented by a single switch responsive to a single environmental factor or responsible to an environmental factor as well as the conscious manual decision of the surgeon. Alternatively, the signal can be implemented with two switches each dealing with one of the environmental factor or the surgeon's conscious choice.

Given these wide variations, which are all within the scope of this concept, one is cautioned not to restrict the invention to the embodiments which have been specifically disclosed and illustrated, but rather encouraged to determine the scope of the invention only with reference to the following claims.

We claim:

1. A trocar system for penetrating a tissue wall in order to provide access for instruments extending into a body cavity of a patient, comprising:
   an obturator having a shaft with a blunt distal tip;
   a cannula having a working channel adapted to removably receive the obturator and to receive the instruments after the obturator has been removed from the cannula;
   a cutting element disposed at the blunt distal tip of the obturator and extending beyond the cannula when the obturator is disposed in the cannula, the cutting element having properties for being electrically energized to cut tissue;
   a power generator for generating a cutting signal;
   conduction means for conducting the cutting signal from the power generator to the cutting element at the blunt tip of the obturator; and
   means responsive to penetration of the tissue wall for inhibiting further electrical energizing of the cutting element in order to prevent further cutting of tissue by the cutting element.

2. The trocar system recited in claim 1 wherein the inhibiting means comprises means for inhibiting generation of the cutting signal by the power generator.

3. The trocar system recited in claim 2 wherein the electrical generator comprises:
   a power electrode;
   a control electrode; and
   a conductor operable to provide continuity between the power electrode and the control electrode in order to activate the generator to produce the cutting signal.

4. The trocar system recited in claim 3 wherein the inhibiting means further comprises a switch disposed in the conductor of the generator and operable to break continuity between the power electrode and the control electrode to inhibit generation of the cutting signal by the electrode generator.

5. The trocar system recited in claim 1 wherein the inhibiting means comprises means for inhibiting conduction of the cutting signal by the conduction means between the electrical generator and the cutting element at the blunt tip of the obturator.

6. A trocar system for penetrating a tissue wall of a patient, in order to provide access for instruments extending into a body cavity of the patient, comprising:
   an obturator having a shaft with a blunt distal tip;
   a cannula having a working channel adapted to removably receive the obturator and to receive the instruments after the obturator has been removed from the cannula;
   a cutting element disposed at the blunt distal tip of the obturator and having properties for being electrically energized to cut tissue;
   first means operatively connected to the cutting element for electrically energizing the cutting element; and
   second means responsive to a particular condition representative of penetration of the tissue wall by the blunt distal tip of the obturator for inhibiting further cutting of tissue by the cutting element.

7. The trocar system recited in claim 6 further comprising:
   lockout means responsive to operation of the second means for preventing further operation of the energizing means; and
   overriding means manually operable for overriding operation of the lockout means to permit further cutting of the tissue in the absence of the particular condition.

8. The trocar recited in claim 6 wherein the second means includes means responsive to a static condition which is present at the inner surface of the tissue wall for inhibiting further cutting by the cutting element.

9. The trocar system recited in claim 8 wherein the second means includes means responsive to pneumoperitoneum pressure within the cavity for inhibiting further cutting by the cutting element.

10. The trocar system recited in claim 8 wherein the second means includes means dependent on the presence of tissue within the tissue wall and the absence of tissue beyond the inner surface of the tissue wall for inhibiting further cutting by the cutting element.

11. The trocar system recited in claim 6 wherein the second means includes means responsive to a dynamic condition which first occurs in proximity to the inner surface of the wall, for inhibiting further cutting by the cutting element.

12. The trocar system recited in claim 11 wherein the second means includes means responsive to an absence of force resisting movement of the distal tip into the cavity for inhibiting further cutting by the cutting element.

13. A trocar system for penetrating wall having an interior surface defining a body cavity of a patient, comprising:
   an obturator having a shaft with a blunt distal tip;
   a cutting element disposed at the distal tip and having properties for being energized to cut tissue;

means for being electrically energizing the cutting tip;

a switch including in the energizing means and having an open state permitting energizing of the cutting tip and a closed state inhibiting energizing of the cutting tip;

an electrically sensor disposed at the distal tip and responsive to conditions present when the distal tip is in proximity to the inner surface of the tissue wall to provide a penetration signal; to automatically switch to the open state, thereby inhibiting further cutting by the cutting element.

14. The trocar system recited in claim 13 wherein the sensor is an optical sensor.

15. The trocar system recited in claim 14 wherein the optical sensor is an infrared sensor.

16. The trocar system recited in claim 13 wherein the sensor is an electrical sensor.

17. The trocar system recited in claim 16 wherein the electrical sensor is an impedance sensor.

18. The trocar system recited in claim 13 wherein the sensor is a mechanical sensor.

19. The trocar system recited in claim 18 wherein the mechanical sensor is a pressure sensor.

20. An electrosurgical trocar system for penetrating a tissue wall in order to provide access for instruments extending into a body cavity of a patient, comprising:

an electrical generator producing an electrical power signal;

an electrosurgical trocar operatively connected to the electrical generator and including an obturator having a distal tip responsive to the electrical power signal of the generator to cut the tissue of the wall as the obturator penetrates the wall;

a cannula having a working channel adapted to removably receive the obturator and to receive the instruments after the obturator has been removed from the cannula; and a cutoff circuit included in one of the electrical generator and electrosurgical trocar, the cutoff circuit being responsive to full penetration of the wall by the distal tip of the electrosurgical trocar to inhibit the electrical power signal produced by the electrical generator and to prevent further cutting of the tissue by the distal tip.

21. The electrosurgical trocar system recited in claim 20 wherein the cutoff circuit comprises:

a sensor responsive to an environmental condition present when the distal tip is in proximity to the inner surface of the wall, to provide a cutoff signal; and means responsive to the cutoff signal to inhibit the electrical power signal.

22. The electrosurgical trocar system recited in claim 21 wherein the means responsive to the cutoff signal includes:

the series combination of the first switch and a second switch operable to introduce the electrical power signal to the distal tip;

the first switch being automatically responsive to the cutoff signal to inhibit introduction of the power signal to the distal tip; and the second switch being manually operable to inhibit introduction of the electrical power signal to the distal tip.

23. The electrosurgical trocar system recited in claim 22 wherein the sensor is an electrical interference receiver and the environmental condition is the absence of electrical interference at the distal tip.

24. An electrosurgical trocar system for penetrating a body wall having an inner surface defining a body cavity, the system comprising:

an electrical generator having a power electrode and properties for producing an electrical power signal;

a control circuit included in the generator;

switch means included in the control circuit of the generator and having a closed state enabling presentation of the power signal on the power electrode and an open state inhibiting presentation of the power signal on the power electrode;

an electrosurgical trocar operatively connected to the generator and having a distal tip carrying a cutting element, the cutting element being responsive to the power signal from the generator to penetrate the body wall;

an electric sensor operatively connected to said switch means and having characteristics for sensing an environmental condition which exists when the distal tip of the trocar is in proximity to the inner surface of the wall, the sensor being responsive to the environmental condition for providing a cutoff signal; and the switch means being responsive to the cutoff signal from the sensor for automatically assuming the open state to inhibit further cutting by the cutting element.

25. The electrosurgical trocar system recited in claim 24 wherein the switch means includes:

a first switch having an open state and a closed state, the first switch being responsive to the cutoff signal from the sensor to assume the open state;

a second switch in series with the first switch and being manually operable between an open state and a closed state; and the switch means having the closed state only when both the first switch and the second switch are in their respective closed states.

26. The electrosurgical trocar system recited in claim 25 wherein the first switch maintains the open state even in the absence of the cutoff signal until the second switch is manually operated to the open state.

27. The electrosurgical trocar system recited in claim 25 wherein the first switch consecutively assumes a first state, a closed state, and a reset state, the first switch automatically moves from the open state to the closed state in response to absence of the cutoff signal and automatically moves from the closed state to the reset state in response to the presence of the cutoff signal, and the switch means further comprises:

reset means manually operable to move the first switch from the reset state to the open state.

28. The electrosurgical trocar system recited in claim 27 wherein the reset means is included in the second switch and is manually operated when the second switch is moved from its closed state to its open state.

29. A trocar system for penetrating a tissue wall of a patient, comprising:

a trocar including a housing and a cannula;

an obturator having a handle, and a shaft extending from the handle, the shaft having a blunt distal tip and being adapted for insertion through the housing and the cannula of the trocar;

an electrical actuated cutting element disposed at the distal tip of the obturator;

means included in the obturator for moving the cutting element through the tissue wall;

a sensor included in the obturator and responsive to a particular condition representative of penetration of the tissue wall by the cutting element to provide an electrical cutoff signal; and a logic circuit responsive to the cutoff signal of the sensor for inhibiting further cutting of the tissue by the cutting element of the obturator.

30. The trocar system recited in claim 29 wherein the logic circuit includes:

a switch having first and second electrodes, an actuator and a lockout element;

the lockout element having a first position in aligned relationship with the actuator and lockout relationship with the first electrode, a second position permitting contact between the first electrode and the second electrode to facilitate cutting by the cutting element, and a third position in lockout relationship with the first electrode and misaligned relationship with the actuator; and the actuator being operable to reset the switch by moving the lockout element from the third position to the first position.

31. The trocar system recited in claim 30 wherein the actuator includes means disposed between at least a portion of the handle and the switch responsive to movement of the handle of the obturator toward the housing of the trocar to move the switch from the third position to the first position.

32. A trocar system for penetrating a tissue barrier of a patient, comprising:

a cannula having a proximal end and a distal end;

an obturator adapted for removable disposition within the cannula and having a shaft with a blunt cutting tip adapted to cut the tissue barrier;

logic means for electrically controlling the cutting of the blunt cutting tip;

cutoff means included in the logic means and responsive to a condition representative of penetration of the tissue barrier by the cutting tip to inhibit further cutting by the blunt cutting tip; and reset means included in the logic means and manually operable for overriding the cutoff means to permit further cutting by the blunt cutting tip of the obturator.

33. The trocar system recited in claim 32 wherein the obturator includes a shield mounted on and slidable along the obturator shaft and the cutoff means includes a cutoff mechanism responsive to the condition to slide the shield along the obturator shaft to cover the cutting tip.

34. The trocar system recited in claim 32 wherein the cutting tip includes an electrosurgical element energizable to cut the tissue barrier.

35. The trocar system recited in claim 34 wherein the cutoff means includes a mechanism responsive to the condition to inhibit further energizing of the electrosurgical element.

36. The trocar system recited in claim 34 further comprising a sensor responsive to the condition representative of penetration to provide an electrical signal; wherein the cutoff means is responsive to the signal from the sensor to inhibit further cutting by the electrosurgical element; and the reset means is manually operable in the absence of the signal from the sensor to override the cutoff means.

37. A method for controlling the cutting of an electrical actuated tissue barrier by a blunt cutting tip disposed at the distal end of a trocar obturator, comprising the steps of:

cutting the tissue barrier with the blunt cutting tip of the obturator;

controlling the cutting of the tissue barrier by the blunt cutting tip through operation of a logic circuit;

sensing a condition representative of substantially complete penetration of the tissue barrier by the blunt cutting tip;

automatically inhibiting further cutting of the cutting tip due to operation of the logic circuit in response to the sensing of the condition; and resetting the logic circuit to permit further cutting of the tissue barrier.

38. The method recited in claim 37 further comprising the steps of:

providing the obturator with a shaft and a shield movable relative to the shaft to cover the cutting tip; and during the inhibiting step moving the shield relative to the shaft to cover the cutting tip and thereby inhibit further cutting of the tissue barrier.

39. The method recited in claim 37 further comprising the steps of:

providing the cutting tip in the form of an electrosurgical element at the distal end of the obturator;

during the cutting step energizing the electrosurgical element to cut the tissue barrier; and during the inhibiting step de-energizing the electrosurgical element in response to the condition to inhibit further cutting of the tissue barrier by the electrosurgical element.

40. The method recited in claim 37 further comprising the steps of:

providing a conductor for energizing the electrosurgical element;

providing a switch in the logic circuit, the switch having a closed state permitting energizing of the electrosurgical element through the conductor and an open state inhibiting the energizing of the electrosurgical element through the conductor;

during the inhibiting step automatically moving the switch to the open state to inhibit energizing of the electrosurgical element; and during the resetting step manually moving the switch to the closed state to energize the electrosurgical element and permit further cutting of the tissue barrier.

41. An electrosurgical trocar system for cutting the tissue of a body wall, comprising:

an electrical generator producing an electrical power signal;

an electrosurgical trocar including a housing and a cannula extending from the housing;

an obturator including a handle and a shaft extending from the handle, the shaft of the obturator being adapted for insertion through the cannula of the trocar and having a distal tip responsive to the electrical power signal of the generator to cut the tissue of the wall as the obturator penetrates the wall;

a cutoff circuit included in one of the electrical generator and the electrosurgical trocar, the cutoff circuit being responsive to the full penetration of the body wall by the distal tip of the electrosurgical trocar to inhibit the electrical power signal produced by the electrical generator and to prevent further cutting of the tissue by the distal tip;

a sensor included in the cutoff circuit and responsive to an environmental condition present when the distal tip is in proximity to an inner surface of the wall, to provide a cutoff signal;

means included in the cutoff circuit and responsive to the cutoff signal for inhibiting the electrical power signal, the inhibiting means including a first switch and a second switch in series combination and operable to introduce the electrical power signal to the distal tip;

the first switch being automatically responsive to the cutoff signal to inhibit introduction of the power signal to the distal tip; and the second switch being disposed in the obturator handle and manually operable by squeezing the handle of the obturator against the housing of the trocar to inhibit introduction of the electrical power signal to the distal tip.

* * * * *